(12) United States Patent
Nakai et al.

(10) Patent No.: US 8,538,110 B2
(45) Date of Patent: Sep. 17, 2013

(54) MEDICAL X-RAY CT IMAGING APPARATUS, MEDICAL X-RAY CT IMAGE DISPLAY DEVICE, AND MEDICAL X-RAY CT IMAGE DISPLAY METHOD

(75) Inventors: Teruji Nakai, Kyoto (JP); Kouji Yasuda, Kyoto (JP); Tetsuzo Ito, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 134 days.

(21) Appl. No.: 12/736,667

(22) PCT Filed: Apr. 30, 2009

(86) PCT No.: PCT/JP2009/058508
§ 371 (c)(1),
(2), (4) Date: Oct. 28, 2010

(87) PCT Pub. No.: WO2009/133937
PCT Pub. Date: Nov. 5, 2009

(65) Prior Publication Data
US 2011/0038519 A1 Feb. 17, 2011

(30) Foreign Application Priority Data
May 1, 2008 (JP) ................... 2008-119837

(51) Int. Cl.
*G06K 9/00* (2006.01)
(52) U.S. Cl.
USPC ............................................. 382/131
(58) Field of Classification Search
USPC ..... 382/128–134; 128/920–925; 356/39–49; 600/407–414, 424–426; 345/581–618
See application file for complete search history.

(56) References Cited

U.S. PATENT DOCUMENTS

| | | | |
|---|---|---|---|
| 6,263,097 B1 | 7/2001 | Dewaele | |
| 2004/0066877 A1 | 4/2004 | Arai et al. | |
| 2005/0117696 A1 | 6/2005 | Suzuki et al. | |
| 2007/0171886 A1 | 7/2007 | Kuth et al. | |
| 2008/0187095 A1* | 8/2008 | Boone et al. ............... | 378/37 |

FOREIGN PATENT DOCUMENTS

| | | |
|---|---|---|
| EP | 1 372 116 A | 12/2003 |
| JP | S54-113292 | 9/1979 |
| JP | H07-303632 | 11/1995 |
| JP | 2001-333898 | 12/2001 |
| JP | 2006-149446 | 6/2006 |
| JP | 2006-187422 | 7/2006 |

(Continued)

OTHER PUBLICATIONS

"VoxeLine: a software program for . . . . " written by Barrou Diallo et al. in the Computerized Medical Imaging and Graphics of Elsevier Science Ltd in 1998, p. 275-289.

(Continued)

*Primary Examiner* — Atiba O Fitzpatrick
(74) *Attorney, Agent, or Firm* — DLA Piper LLP (US)

(57) ABSTRACT

A medical X-ray CT imaging apparatus, a medical X-ray CT image display device, and a medical X-ray CT image display method which perform CT imaging of living organs symmetrically located with respect to a predetermined plane and display CT images thereof. This is a method of displaying a medical X-ray CT image, where a CT image obtained by X-ray CT imaging, using a cone beam (B), of a first living organ and a second living organ which are symmetrically located with respect to the predetermined plane. In the present invention, the CT image of the first living organ and that of the second living organ are displayed for comparison on one display screen of a display means.

10 Claims, 29 Drawing Sheets

(56) References Cited

FOREIGN PATENT DOCUMENTS

| JP | 3807833 | 8/2006 |
| JP | 2007-29166 | 2/2007 |
| JP | 3926120 | 6/2007 |
| WO | WO 2007/102510 A | 9/2007 |

OTHER PUBLICATIONS

"Visualization in biomedical computing" written by Richard A. Robb in the Parallel Computing of Elsevier Science Ltd. in 1999, p. 2067-2110.

"Three-Dimensional Diagnosis & Treatment Planning: The Use of 3D Facial . . ." by William E. Harrell in the Australasian Dental Practice, Jul./Aug. 2007, pp. 102-113.

"Clinical Technology Course Usefulness of . . ." by Kazuo Maruhashi in the Japan Radiation Technology Academy Magazine, Oct. 20, 2003, vol. 59 No. 10, pp. 1222-1228.

"Diagnostic Imaging of Dental/Oral Surgery Region Correction and Application to . . ." by Kazuyuki Araki in the Image Information Medial, Jun. 1, 2004, vol. 36 No. 7, pp. 682-687.

* cited by examiner

F I G. 1
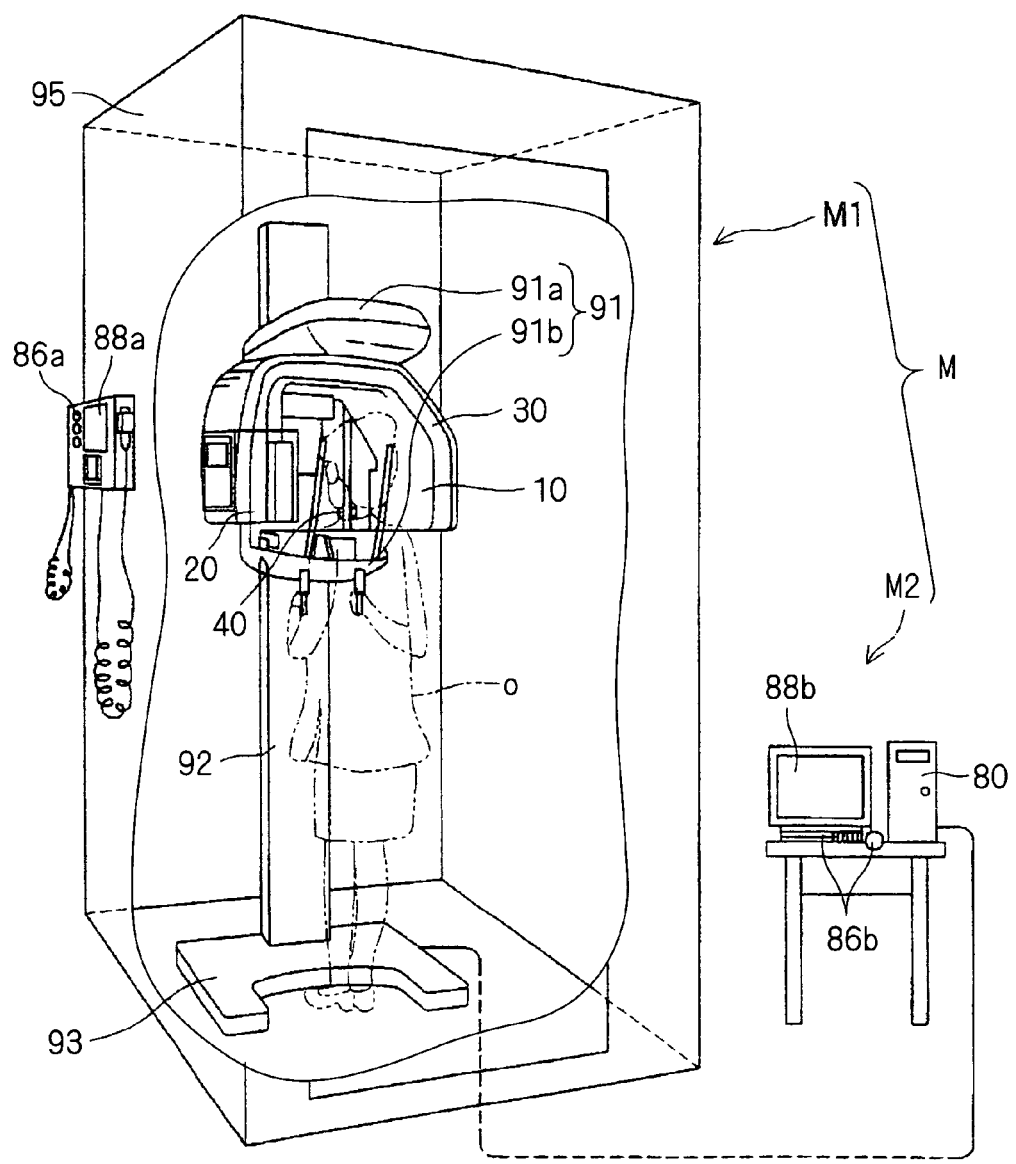

F I G . 3 3
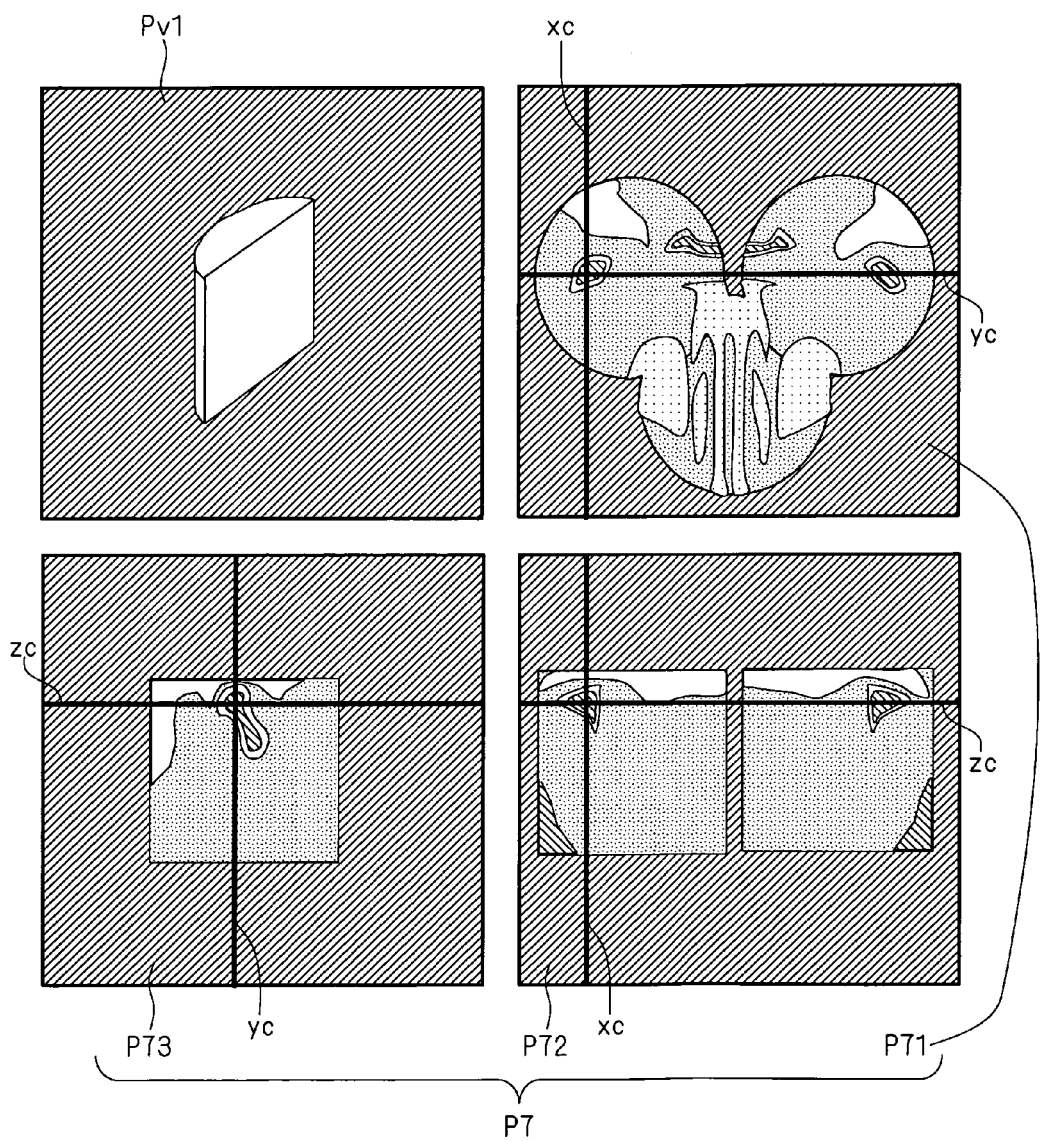

F I G . 3 4
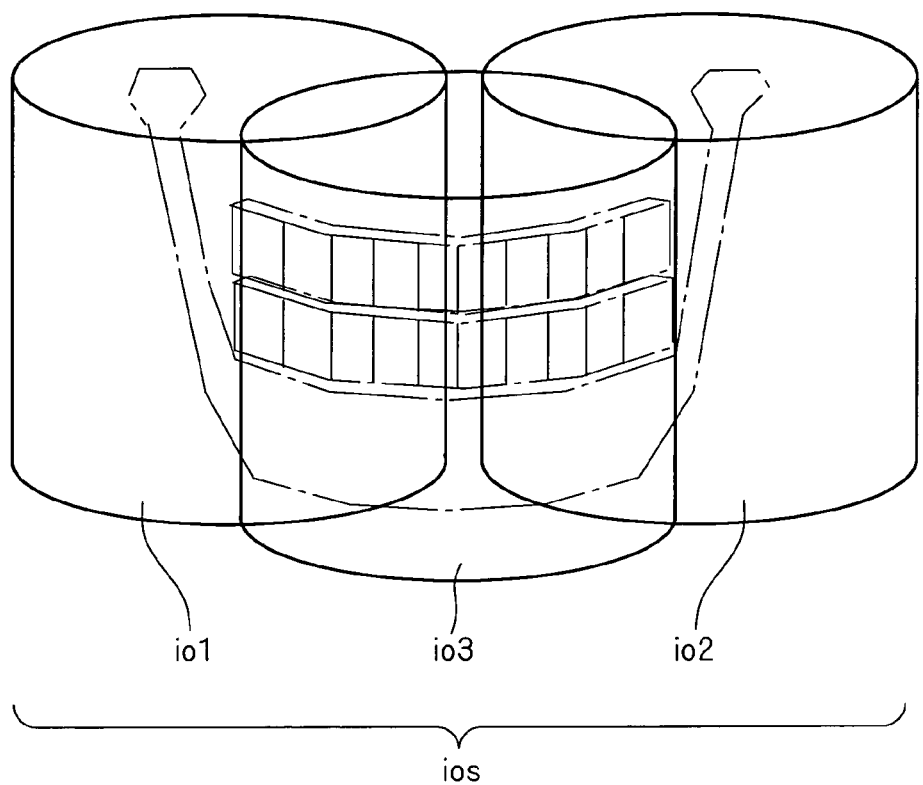

MEDICAL X-RAY CT IMAGING APPARATUS, MEDICAL X-RAY CT IMAGE DISPLAY DEVICE, AND MEDICAL X-RAY CT IMAGE DISPLAY METHOD

TECHNICAL FIELD

The present invention relates to a medical X-ray CT imaging apparatus, a medical X-ray CT image display device, and a medical X-ray CT image display method. More particularly, the present invention relates to a medical X-ray CT imaging apparatus, a medical X-ray CT image display device, and a medical X-ray CT image display method which perform CT imaging of living organs symmetrically located with respect to a predetermined plane and display CT images thereof.

BACKGROUND ART

In recent years, the development of medical X-ray CT imaging apparatuses has advanced and many apparatuses having provisions for imaging in dentistry or imaging of head including otolaryngological regions and the like have been developed and manufactured. In the field of dental X-ray CT imaging apparatus, apparatuses for combined use of not only CT imaging but also panoramic radiography (disclosed in e.g., Japanese Patent No. 3807833) have been developed. Japanese patent Application Laid Open Gazette No. 54-113291 discloses an example of old-type medical X-ray CT imaging apparatus which performs film radiography. The medical X-ray imaging apparatus disclosed in Japanese Patent Application Laid Open Gazette No. 54-113292 is a dental panoramic radiography apparatus having a function of temporomandibular joint radiography, which is capable of both radiography of temporomandibular joints in open and closed states and panoramic radiography. The X-ray imaging apparatus disclosed in Japanese Patent Application Laid Open Gazette No. 54-113292, however, is not an X-ray CT imaging apparatus and therefore the apparatus cannot reconstruct the cross sections of the temporomandibular joints from an arbitrary direction.

As another example of medical X-ray CT imaging apparatus, Japanese Patent Application Laid-Open Gazette No. 2006-149446 discloses an X-ray CT imaging apparatus, which is used for diagnosis of organs located at left and right sides of a spine. The X-ray CT imaging apparatus disclosed in Japanese Patent Application Laid-Open Gazette No. 2006-149446 has a technology for extracting portions which are symmetrically located at left and right sides with a spinal cord as a center line. Japanese Patent No. 3926120 discloses an apparatus for specifying a region of interest on a schematic view of a subject as an imaging target region and performing X-ray CT imaging of the imaging target region.

DISCLOSURE OF INVENTION

In order to perform X-ray CT imaging of living organs (for example, temporomandibular joints or otolaryngological regions) which are symmetrically located with respect to a predetermined plane (for example, a section plane including a median line by which a living body is divided into left and right sides or an occlusal surface of a head), conventional medical X-ray CT imaging apparatuses need to separately capture the respective images of the living organs or perform an additional operation of extracting symmetrically-located portions out of the captured CT images. Further, in order to compare the CT images of the living organs which are symmetrically located with respect to a predetermined plane with each other, the conventional medical X-ray CT imaging apparatus, the conventional medical X-ray CT image display device and the conventional medical X-ray CT image display method require operator's operation for displaying the CT images for comparison and therefore cannot support efficient diagnoses or effective explanations for patients.

It is an object of the present invention to provide a medical X-ray CT imaging apparatus, a medical X-ray CT image display device, and a medical X-ray CT image display method which perform CT imaging of living organs which are symmetrically located with respect to a predetermined plane and display CT images thereof.

In order to solve the above problems, a medical X-ray CT image display method according to a first aspect of the present invention is a method of displaying medical X-ray CT images which are CT images obtained by X-ray CT imaging, using a cone beam, of a first living organ and a second living organ which are located symmetrically with respect to a predetermined plane, and in the method, the CT image of the first living organ and the CT image of the second living organ are displayed on one display screen for comparison.

Since the respective CT images of the first living organ and the second living organ which are symmetrically located with respect to the predetermined plane can be thereby displayed in one display screen for comparison, the viewability of the first and second living organs increases and this produces the effect of supporting efficient diagnoses and effective explanations for patients.

According to a second aspect of the present invention, in the medical X-ray CT image display method of the first aspect, when an imaging region of one of the first living organ and the second living organ is specified and an arbitrary cross sectional CT image thereof is displayed, a corresponding cross sectional CT image of the imaging region of the other living organ, which is located symmetrically to the specified imaging region with respect to the predetermined plane, is automatically displayed on the same display screen for comparison.

By specifying the imaging region of one of the first and second living organs and displaying the arbitrary cross sectional CT image thereof, the corresponding cross sectional CT image of the imaging region of the other living organ can be also automatically displayed on the same display screen for comparison. An operator can thereby omit the operation for specifying both imaging regions, and this advantageously results in a simple operation.

According to a third aspect of the present invention, in the medical X-ray CT image display method of the second aspect, arbitrary three cross sections which are orthogonal to one another are set with respect to each of the CT images of the first living organ and the second living organ, the three cross sections and cursors associated with the three cross sections are displayed for each of the first and second living organs, and by moving one of the cursors in any one of the three cross sections of one of the first and second living organs, the cursors in the three cross sections of the other living organ are also moved symmetrically with respect to the predetermined plane and a cross sectional CT image obtained at the position of the cursor with respect to each of the first living organ and the second living organ is displayed.

Since the cross sectional CT images at the positions of the cursors can be displayed by moving the cursors associated with the three cross sections, it is possible to display the imaging region of the operator in more detail and this produces the effect of supporting efficient diagnoses.

According to a fourth aspect of the present invention, the medical X-ray CT image display method of any one of the first to third aspects further comprises the step of combining respective CT imaging data of the first living organ and the second living organ and CT imaging data of a third living organ located between the first living organ and the second living organ to synthesize a CT image and displaying the CT image.

When the CT imaging of the third living organ as well as the first and second living organs is performed, a CT image is synthesized by combining the respective CT imaging data of the first, second and third living organs and the CT image is displayed. This allows high visibility for recognition of the positions of these three living organs.

A medical X-ray CT image display device according to a fifth aspect of the present invention comprises a CT image acquisition part for acquiring CT images obtained by X-ray CT imaging, using a cone beam, of a first living organ and a second living organ which are symmetrically located with respect to a predetermined plane, and a display part for displaying the CT image of the first living organ and the CT image of the second living organ which are acquired by the CT image acquisition part, on one display screen for comparison.

Since the display part displays the respective CT images of the first living organ and the second living organ which are symmetrically located with respect to the predetermined plane on one display screen for comparison, the viewability of the first and second living organs increases and this produces the effect of supporting efficient diagnoses and effective explanations for patients.

According to a sixth aspect of the present invention, the medical X-ray CT image display device of the fifth aspect further comprises a storage part for storing the CT image of the first living organ and the CT image of the second living organ which are displayed for comparison while associating the CT images with each other, and in the medical X-ray CT image display device, the display part displays the CT images of the first living organ and the second living organ which are stored in the storage part and associated with each other, for comparison.

Since the storage part stores the CT image of the first living organ and the CT image of the second living organ while associating these CT images with each other, it is possible to manage the CT images of the first and second living organs as a pair of data, and this produces the effect of simplifying data management.

According to a seventh aspect of the present invention, in the medical X-ray CT image display device of the fifth or sixth aspect, when the display part specifies an imaging region of one of the first living organ and the second living organ and displays an arbitrary cross sectional CT image thereof, the display part also automatically displays a corresponding cross sectional CT image of the imaging region of the other living organ, which is located symmetrically to the specified imaging region with respect to the predetermined plane, on the same display screen for comparison.

By specifying the imaging region of one of the first and second living organs and displaying the arbitrary cross sectional CT image thereof, the corresponding cross sectional CT image of the imaging region of the other living organ can be also automatically displayed on the same display screen for comparison. The operator can thereby omit the operation for specifying both imaging regions, and this advantageously results in a simple operation.

According to an eighth aspect of the present invention, in the medical X-ray CT image display device of the seventh aspect, the display part displays arbitrary three cross sections orthogonal to one another which are set with respect to each of the CT images of the first living organ and the second living organ and cursors associated with the three cross sections of each of the CT images, and by moving one of the cursors in any one of the three cross sections of one of the first and second living organs, the display part also moves the cursors in the three cross sections of the other living organ symmetrically with respect to the predetermined plane and displays a cross sectional CT image obtained at the position of the cursor with respect to each of the first living organ and the second living organ.

Since the cross sectional CT images at the positions of the cursors can be displayed by moving the cursors associated with the three cross sections, it is possible to display the imaging region of the operator in more detail and this produces the effect of supporting efficient diagnoses.

According to a ninth aspect of the present invention, in the medical X-ray CT image display device of any one of the sixth to eighth aspects, the first living organ and the second living organ are temporomandibular joints or otolaryngological regions.

Since the temporomandibular joints or the living organs of the otolaryngological regions are living organs symmetrically located with respect to a predetermined plane in many cases, the device has the effect of supporting efficient diagnoses.

According to a tenth aspect of the present invention, in the medical X-ray CT image display device of the ninth aspect, the first living organ and the second living organ are temporomandibular joints, and the CT images of the first living organ and the second living organ are moving images from an open state to a closed state.

Since the CT images are moving images from the open state to the closed state, it is possible to make a diagnosis while observing actual movements of the living organs, and therefore the device has the effect of supporting efficient diagnoses.

According to an eleventh aspect of the present invention, in the medical X-ray CT image display device of the fifth aspect, the CT images of the first living organ and the second living organ are cross sectional images at positions in plane symmetry with respect to the predetermined plane or images in a direction of mirror symmetry with respect to the predetermined plane.

Since the respective CT images of the first and second living organs are cross sectional images at the positions in plane symmetry with respect to the predetermined plane or images in a direction of mirror symmetry with respect to the predetermined plane, it is possible to clarify the contrast between the first and second living organs for diagnosis and explanation for a patient.

According to a twelfth aspect of the present invention, in the medical X-ray CT image display device of the fifth aspect, a CT image is synthesized by combining respective CT imaging data of the first living organ and the second living organ and CT imaging data of a third living organ located between the first living organ and the second living organ displayed.

When the CT imaging of the third living organ as well as the first and second living organs is performed, a CT image is synthesized by combining the respective CT imaging data of the first, second and third living organs and the CT image is displayed. This allows high visibility for recognition of the positions of these three living organs.

A medical X-ray CT imaging apparatus according to a thirteenth aspect of the present invention comprises an X-ray source for generating a cone beam, an X-ray detection part for detecting the cone beam, a supporting part for arranging the X-ray source and the X-ray detection part to be opposed to each other with a subject positioned therebetween, a subject holding part for holding the subject, a rotation driving part for driving the supporting part and the subject holding part to rotate relative to each other, an imaging region specifying part for specifying respective imaging regions of the first living organ and the second living organ which are symmetrically located with respect to a predetermined plane, an image processing part for reconstructing respective CT images of the first living organ and the second living organ on the basis of an electrical signal obtained by the X-ray detection part through cone beam CT imaging of regions including the imaging regions specified by the imaging region specifying part, and a display part for displaying the CT images of the first living organ and the second living organ which are obtained by the calculation part, on one display screen for comparison.

Since the image processing part reconstructs respective CT images of the first living organ and the second living organ on the basis of the electrical signal obtained by the X-ray detection part through cone beam CT imaging of regions including the imaging regions specified by the imaging region specifying part and the display part displays both the CT images on one display screen for comparison, the CT images of both the first living organ and the second living organ can be acquired by one cone beam CT imaging and this produces the effect of cutting the time for imaging and reducing the time required for diagnosis of a patient. Further, since the medical X-ray CT imaging apparatus of the tenth aspect displays the respective CT images of the first and second living organs on one display screen for comparison, the viewability of the first and second living organs increases and this produces the effect of supporting efficient diagnoses.

According to a fourteenth aspect of the present invention, in the medical X-ray CT imaging apparatus of the thirteenth aspect, the imaging region specifying part displays an illustration for specifying at least the first living organ and the second living organ on an operation panel, to specify the imaging regions on the basis of the illustration.

Since the operator can specify the imaging regions on the basis of the illustration of the living organs, the apparatus has the effect of ensuring easy specification of the imaging regions as imaging targets.

According to a fifteenth aspect of the present invention, the medical X-ray CT imaging apparatus of the thirteenth or fourteenth aspect further comprises an imaging condition changing part for selecting whether the subject is an adult or a child and changing the condition for the cone beam CT imaging according to the selection.

Since the imaging condition changing part selects whether the subject is an adult or a child and changes the imaging condition, the apparatus has the effect of achieving automatic control on the tube current, the tube voltage, and the like of an optimal X-ray power supply. In the medical X-ray CT imaging apparatus of the thirteenth aspect, by selecting adult or child, it is possible to automatically determine roughly the positions of the first and second living organs, i.e., the respective center positions of the imaging regions (on the basis of the factory setting value).

According to a sixteenth aspect of the present invention, the medical X-ray CT imaging apparatus of any one of the thirteenth to fifteenth aspects further comprises a storage part for storing the CT image of the first living organ and the CT image of the second living organ which are displayed for comparison while associating the CT images with each other.

Since the storage part stores the CT image of the first living organ and the CT image of the second living organ while associating the CT images with each other, it is possible to manage the CT images of the first and second living organs as a pair of data, and therefore the apparatus has the effect of simplifying data management.

According to a seventeenth aspect of the present invention, in the medical X-ray CT imaging apparatus of any one of the thirteenth to sixteenth aspects, when the display part specifies an imaging region of one of the first living organ and the second living organ and displays an arbitrary cross sectional CT image thereof, the display part also automatically displays a corresponding cross sectional CT image of the imaging region of the other living organ, which is located symmetrically to the specified imaging region with respect to the predetermined plane, on the same display screen for comparison.

By specifying the imaging region of one of the first and second living organs and displaying the arbitrary cross sectional CT image, the corresponding cross sectional CT image of the imaging region of the other living organ can be also automatically displayed on the same display screen for comparison. The operator can thereby omit the operation for specifying both the imaging regions, and this advantageously results in a simple operation.

According to an eighteenth aspect of the present invention, in the medical X-ray CT imaging apparatus of the seventeenth aspect, the display part displays arbitrary three cross sections orthogonal to one another which are set with respect to each of the CT images of the first living organ and the second living organ and cursors associated with the three cross sections of each of the CT images, and by moving one of the cursors in any one of the three cross sections of one of the first and second living organs, the display part also moves the cursors in the three cross sections of the other living organ symmetrically with respect to the predetermined plane and displays a cross sectional CT image obtained at the position of the cursor with respect to each of the first living organ and the second living organ.

Since the cross sectional CT images at the positions of the cursors can be displayed by moving the cursors associated with the three cross sections, it is possible to display the imaging region of the operator in more detail and this produces the effect of supporting efficient diagnoses.

According to a nineteenth aspect of the present invention, in the medical X-ray CT imaging apparatus of any one of the thirteenth to eighteenth aspects, the first living organ and the second living organ are temporomandibular joints or otolaryngological regions.

Since the temporomandibular joints or the living organs of the otolaryngological regions are living organs symmetrically located with respect to a predetermined plane in many cases, the apparatus has the effect of supporting efficient diagnoses.

According to a twentieth aspect of the present invention, in the medical X-ray CT imaging apparatus of the nineteenth aspect, the cone beam CT imaging is performed on a left temporomandibular joint which is the first living organ and a right temporomandibular joint which is the second living organ in an open state and a closed state, and the display part displays the open state and the closed state of the left and right temporomandibular joints on one display screen for comparison.

Since the CT images of the open state and the closed state can be displayed on one display screen for comparison, it is possible to make a diagnosis while observing the change between in the open state and in the closed state of the living organs, and therefore the apparatus has the effect of supporting efficient diagnoses.

According to a twenty-first aspect of the present invention, in the medical X-ray CT imaging apparatus of the nineteenth aspect, the CT images of the first living organ and the second living organ are moving images from an open state to a closed state.

Since the CT images are moving images from the open state to the closed state, it is possible to make a diagnosis while observing actual movements of the living organs, and therefore the apparatus has the effect of supporting efficient diagnoses.

According to a twenty-second aspect of the present invention, in the medical X-ray CT imaging apparatus of the thirteenth aspect, the CT images of the first living organ and the second living organ are cross sectional images at positions in plane symmetry with respect to the predetermined plane or images in a direction of mirror symmetry with respect to the predetermined plane.

Since the respective CT images of the first and second living organs are cross sectional images at the positions in plane symmetry with respect to the predetermined plane or images in a direction of mirror symmetry with respect to the predetermined plane, it is possible to clarify the contrast between the first and second living organs for diagnosis and explanation for a patient.

According to a twenty-third aspect of the present invention, in the medical X-ray CT imaging apparatus of the thirteenth aspect, X-ray CT imaging of a third living organ located between the first living organ and the second living organ is further performed, and a CT image is synthesized by combining respective CT imaging data of the first living organ and the second living organ and CT imaging data of the third living organ and displayed.

When the CT imaging of the third living organ as well as the first and second living organs is performed, a CT image is synthesized by combining the respective CT imaging data of the first, second and third living organs and the CT image is displayed. This allows high visibility for recognition of the positions of these three living organs.

According to a twenty-fourth aspect of the present invention, in the medical X-ray CT imaging apparatus of any one of the thirteenth to twenty-third aspects, the predetermined plane is a section plane including a median line by which a living body is divided into left and right sides.

BRIEF DESCRIPTION OF DRAWINGS

FIG. 1 is a schematic view showing a medical X-ray CT imaging apparatus M in accordance with a first preferred embodiment of the present invention;

FIG. 33 is a view showing an example of image display in a case where serial CT imaging is performed on a first living organ, a second living organ, and a third living organ;

FIG. 34 is a view schematically showing synthesized CT imaging data ios; and

Figure 2:
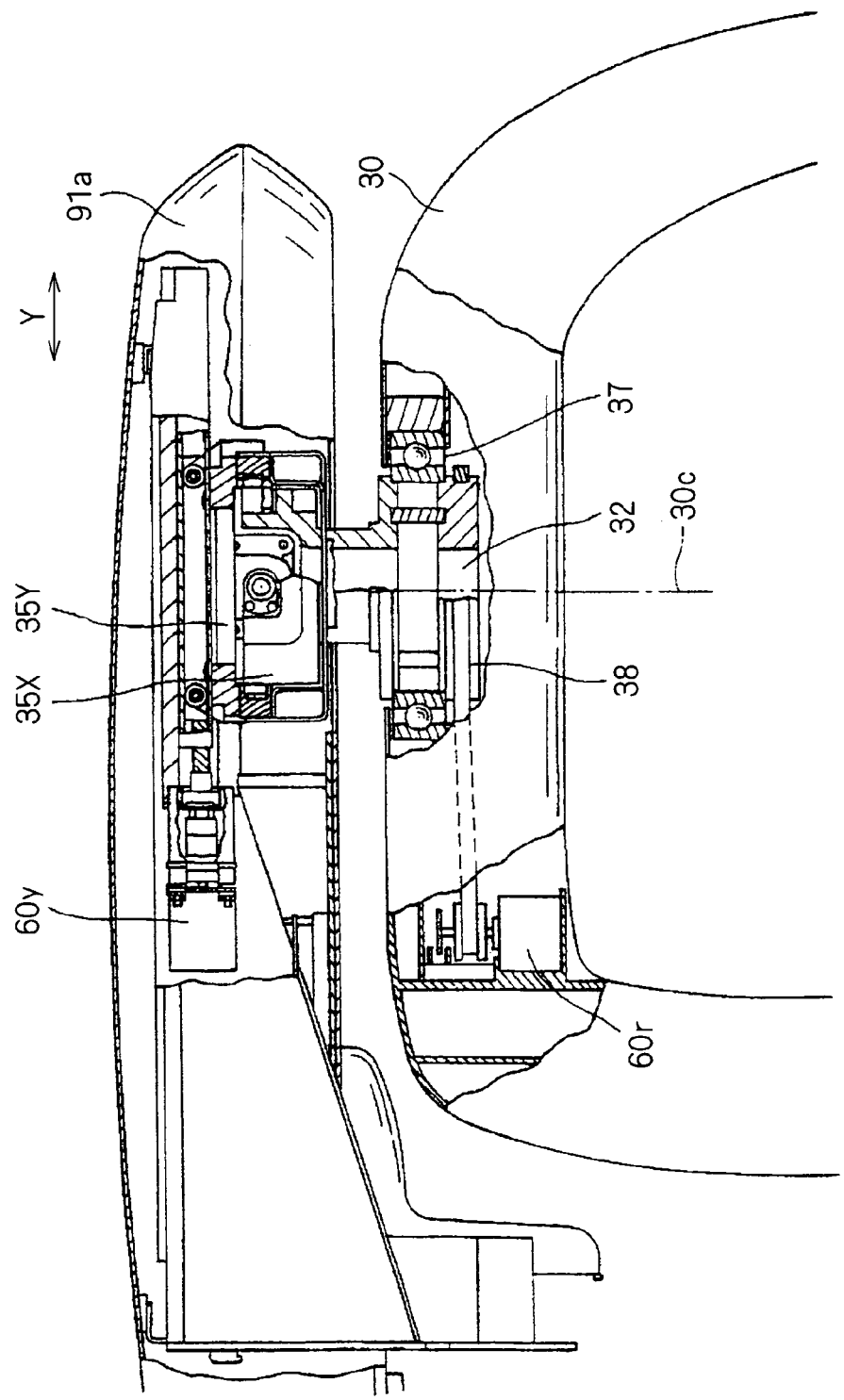
FIGS. 2 to 4 are schematic views showing a supporting part and a driving part of the medical X-ray CT imaging apparatus M in accordance with the first preferred embodiment of the present invention.

BEST MODE FOR CARRYING OUT THE INVENTION (The First Preferred Embodiment)

A medical X-ray CT imaging apparatus in accordance with the first preferred embodiment performs CT imaging of a subject, specifies living organs (for example, temporomandibular joints or otolaryngological regions) which are symmetrically located with respect to a predetermined plane of the subject (for example, a section plane including a median line by which a living body is divided into left and right sides or an occlusal surface of a head) as imaging regions to reconstruct CT images, and displays the CT images of the living organs for comparison. The CT images include a tomography image and a volume rendering image of each of the living organs symmetrically located with respect to the predetermined plane.

FIG. 1 is a view showing a medical X-ray CT imaging apparatus in accordance with the first preferred embodiment. The medical X-ray CT imaging apparatus M of FIG. 1 comprises an X-ray imaging apparatus body M1 and an X-ray image display device M2. The X-ray imaging apparatus body M1 comprises a supporting part 30 which is a rotation arm incorporating a rotation motor, supporting an X-ray generation part 10 and an X-ray detection part 20 which are provided at the ends of the supporting part 30 and opposed to each other. In order to move the supporting part 30 up and down, the supporting part 30 is suspended from an up-and-down moving frame 91. The up-and-down moving frame 91 is provided with respect to a column 92 standing right from a base 93 and has an upper frame 91a from which the supporting part 30 is suspended and a lower frame 91b for holding a subject o, which are configured to form a substantially squared U-shape projecting forward. The up-and-down moving frame 91 is movable up and down by means of a not-shown up-and-down moving mechanism and incorporates an XY table (not shown) for horizontally moving the rotation axis of the supporting part 30.

The lower frame 91b comprises a subject holding part 40 constituted of an ear rod for fixing a human head which is a subject o from the left and right sides, a chin rest for fixing a chin, and the like. The subject o is introduced in the subject holding part 40 at an appropriate position by moving the supporting part 30 up or down in accordance with the height of the subject o. The X-ray imaging apparatus body M1 of FIG. 1 is housed in an X-ray proof chamber 95, and at the outer wall of the X-ray proof chamber 95, attached is an operation panel 86a provided with a small-sized liquid crystal panel serving as a display part 88a. The X-ray image display device M2 of FIG. 1 is configured to transfer data between itself and the X-ray imaging apparatus body M1 via a communication cable. The X-ray image display device M2 is constituted of e.g., a computer and a workstation, and a display device body 80 is provided with a display part 88b formed of a display device such as a liquid crystal monitor or the like and an operation part 86b constituted of a keyboard, a mouse, and the like. Various commands can be given through a mouse pointer operation or the like on characters or images displayed on the display part 88b. The display part 88b may be formed of a touch panel, and therefore the display part 88b also serves as the operation part 86b in this case.

FIG. 2 is a partially sectional view showing the supporting part 30 and the upper frame 91a. The upper frame 91a comprises a table (Y table) 35Y which moves in a fore-and-aft direction (Y direction), a table (X table) 35X which is supported by the Y table 35Y and moves in a horizontal direction (X direction), a Y-axis motor 60y of the Y direction for moving the Y table 35Y in the Y direction, an X-axis motor (not shown) for moving the X table 35X in the X direction relative to the Y table 35Y, and a rotation motor 60r for rotating the supporting part 30 about a rotation axis 30c which is the axis center of an axis 32 coupling the X table 35X and the supporting part 30. A bearing 37 is provided between the axis 32 and the supporting part 30, thereby facilitating the rotation of the supporting part 30 about the axis 32. The rotation motor 60r is fixed inside the supporting part 30 and transmits the rotation force via a belt 38 to the axis 32, to thereby rotate the supporting part 30. The mechanism comprising the axis 32, the bearing 37, the belt 38, and the rotation motor 60r is an exemplary rotation mechanism for rotating the supporting part 30. By driving the three control motors in accordance with a predetermined program, it is possible to move the XY table (35X, 35Y) in the fore-and-aft (Y) direction and the left and right (X) direction while rotating the supporting part 30.

Figure 3:
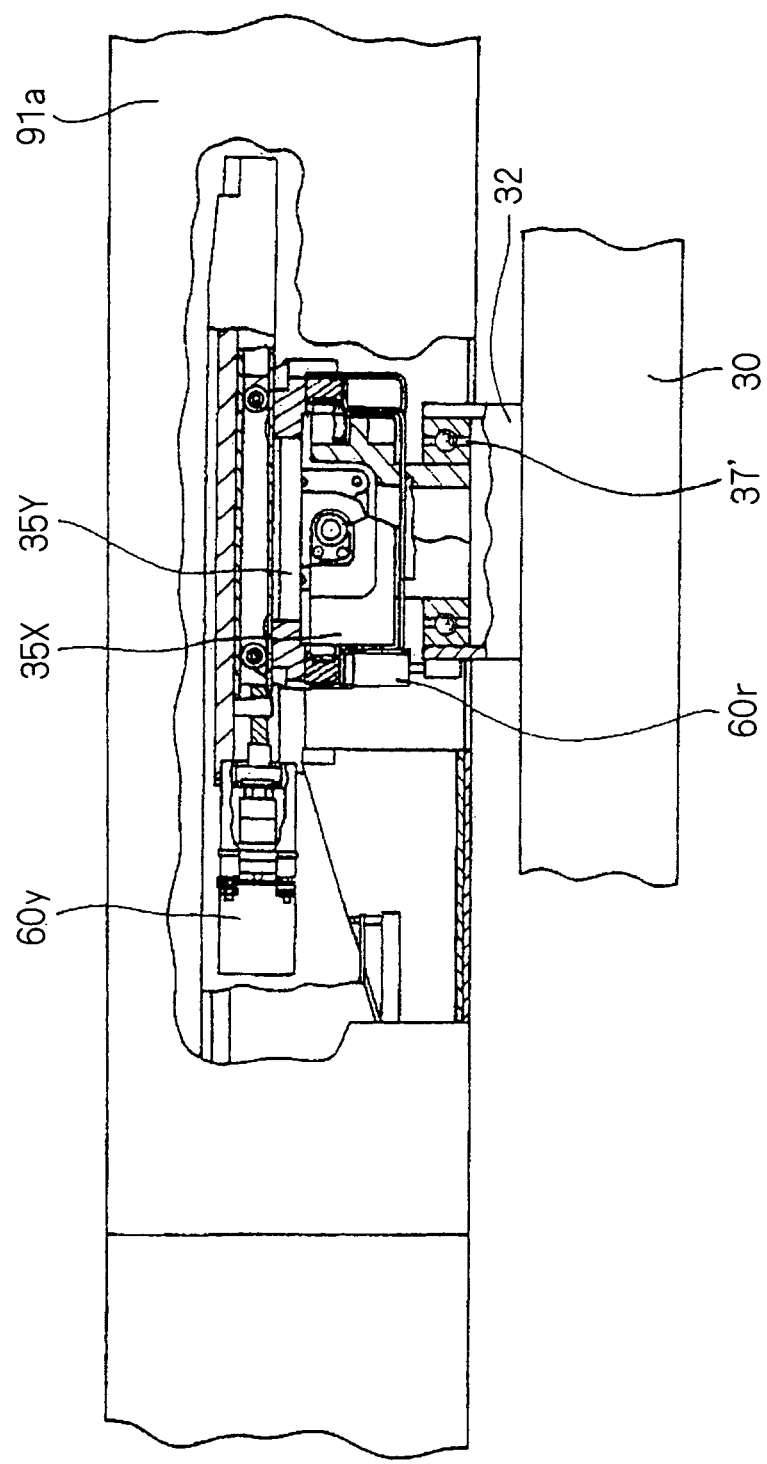

The mechanism of FIG. 2 for rotating and moving the supporting part 30 is an exemplary one. The present invention is not limited to this exemplary mechanism but such a mechanism comprising another supporting part 30 and another upper frame 91a as shown in FIG. 3 may be used. The mechanism of FIG. 3 is mostly the same as that shown in FIG. 2 but different therefrom in the construction of a rotation mechanism for rotating the supporting part 30. The upper frame 91a comprises the table (Y table) 35Y which moves in the fore-and-aft direction (Y direction), the table (X table) 35X which is supported by the Y table 35Y and moves in the horizontal direction (X direction), the Y-axis motor 60y of the Y direction for moving the Y table 35Y in the Y direction, the X-axis motor 60x for moving the X table 35X in the X direction relative to the Y table 35Y, and the rotation motor 60r for rotating the supporting part 30 about the rotation axis 30c which is the axis center of the axis 32 coupling the X table 35X and the supporting part 30. The upper frame 91a of FIG. 3 further comprises the axis 32 coupling the X table 35X and the supporting part 30 and a bearing 37' provided between the axis 32 and the supporting part 30. The rotation axis of the rotation motor 60r comes into contact with the outer perimeter of the axis 32 fixed on the supporting part 30 to transmit the rotation force to the axis 32, whereby the supporting part 30 rotates.

Figure 4:
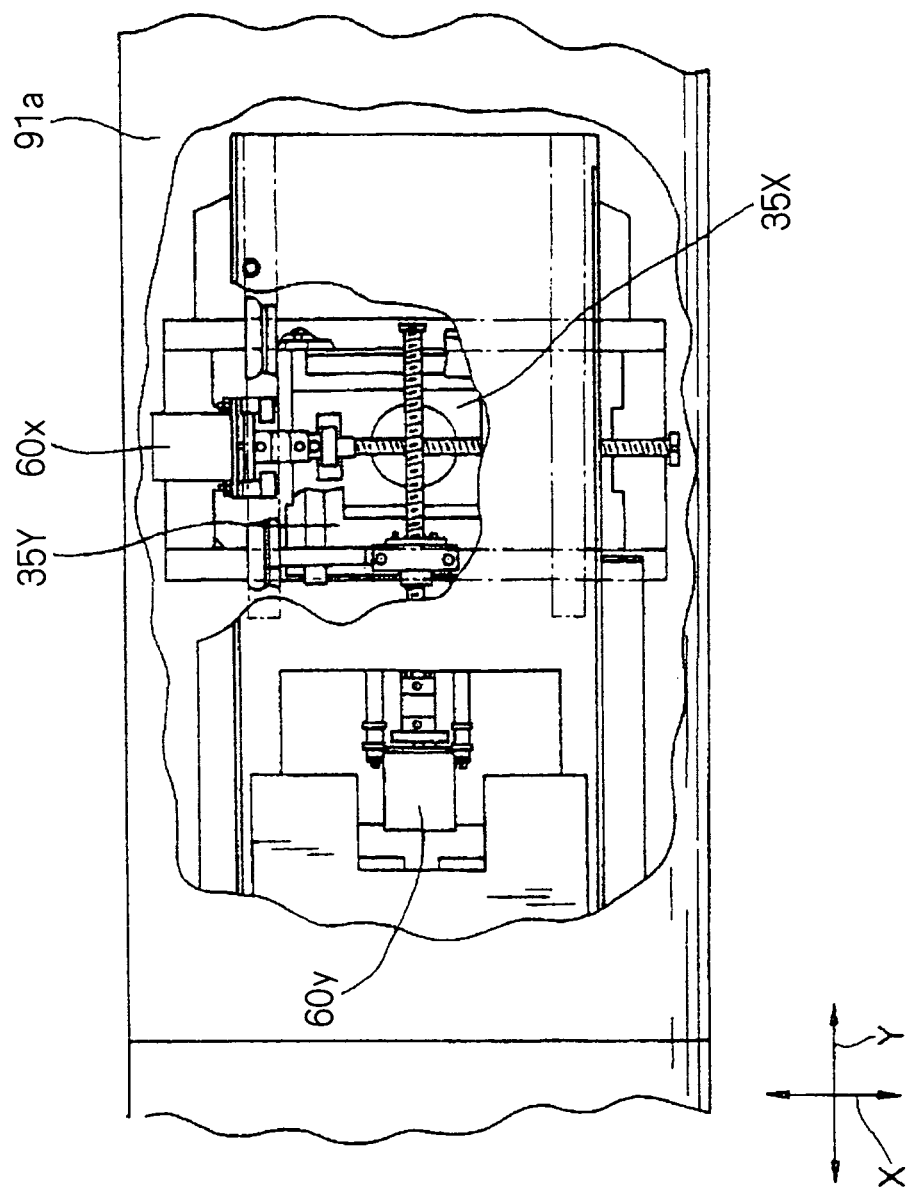

FIG. 4 is a plain view of the XY table (35X, 35Y) shown in FIGS. 2 and 3. FIG. 4 shows the arrangement of the table (Y table) 35Y which moves in the fore-and-aft direction (Y direction), the table (X table) 35X which is supported by the Y table 35Y and moves in the horizontal direction (X direction), the Y-axis motor 60y of the Y direction for moving the Y table in the Y direction, the X-axis motor 60x for moving the X table in the X direction relative to the Y table. In the above-discussed case, for convenience of coordinate calculation for control, the X direction and the Y direction are orthogonal to each other, but the two directions may be crossed at an arbitrary angle, instead of right angle, only if the two-dimensional control can be made.

Figure 5:
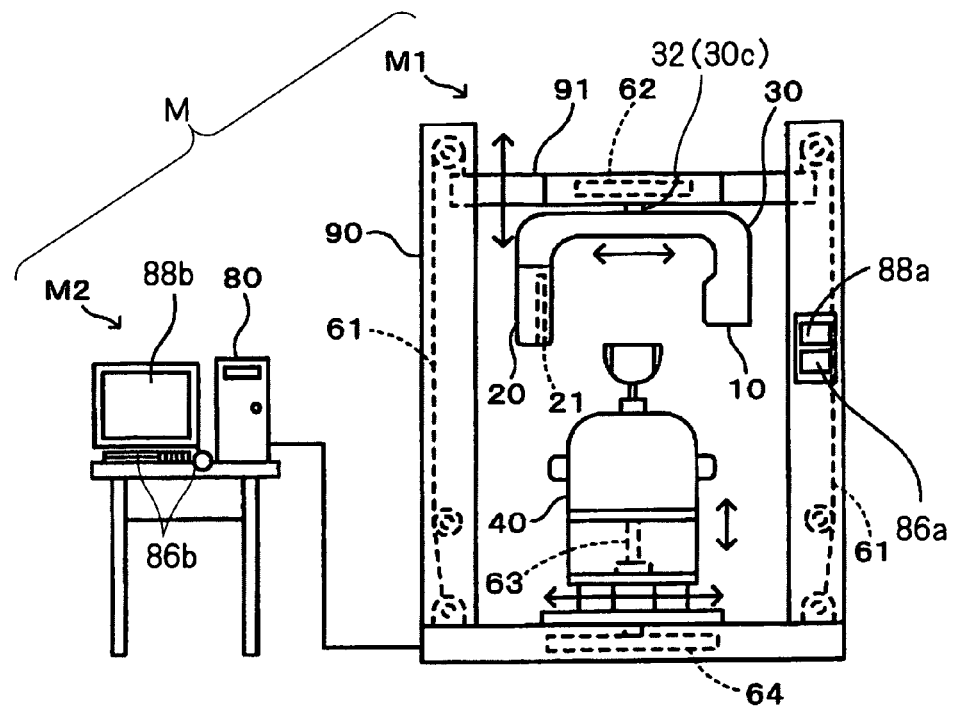
FIG. 5 is an elevational view showing the medical X-ray CT imaging apparatus M in accordance with the first preferred embodiment of the present invention.
Figure 6:
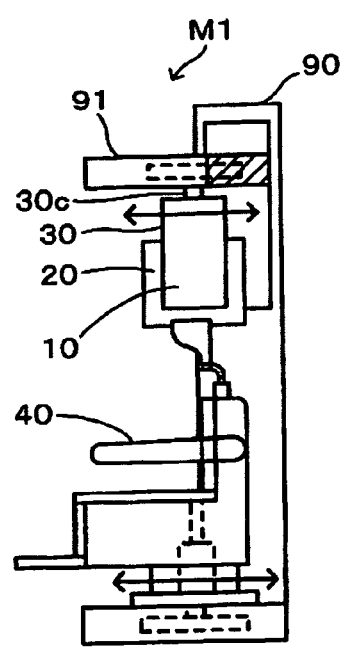
FIG. 6 is a side elevation showing the medical X-ray CT imaging apparatus M in accordance with the first preferred embodiment of the present invention.

The medical X-ray CT imaging apparatus of the present invention is not limited to the medical X-ray CT imaging apparatus M shown in FIG. 1 but may be another medical X-ray CT imaging apparatus M shown in FIGS. 5 and 6. FIG. 5 is an elevational view of another medical X-ray CT imaging apparatus M and FIG. 6 s a side elevation of the medical X-ray CT imaging apparatus M of FIG. 5. The X-ray imaging apparatus body M1 shown in FIGS. 5 and 6 comprises the supporting part 30 which is rotated by the rotation motor 60r (not shown) and supports the X-ray generation part 10 and the X-ray detection part 20 which are provided at the ends of the supporting part 30 and opposed to each other and the subject holding part 40 which is formed like a seat and comprises a headrest or a holder for fixing a human head which is the subject o, and the supporting part 30 and the subject holding part 40 are displaceably attached to a fixed frame 90 formed like an arch.

More specifically, the supporting part 30 is attached to the fixed frame 90 with the up-and-down moving frame 91 interposed therebetween. The up-and-down moving frame 91 which is vertically movable by means of a chain drive part 61 incorporates an XY table 62 for two-dimensionally moving the axis 32 (rotation axis 30c) about which the supporting part 30 is rotated, specifically in this case, for moving the axis 32 horizontally in the X direction and the Y direction. The subject holding part 40 is supported at the bottom thereof from below by a up-and-down moving part 63 which is movable up and down, and the bottom of the fixed frame 90 incorporates an XY table 64 for horizontally moving the up-and-down moving part 63, like the XY table 62. At the column of the fixed frame 90, attached are the display part 88a formed of a liquid crystal monitor, a small-sized liquid crystal panel, or the like and the operation panel 86a comprising a plurality of operation buttons and the like. An X-ray detector 21 is a device for detecting an X-ray, which is attached to the X-ray detection part 20.

Next, the medical X-ray CT imaging apparatus M of the first preferred embodiment will be described with reference to the block diagram of FIG. 7. The medical X-ray CT imaging apparatus M of FIG. 7 comprises the X-ray imaging apparatus body M1 and the X-ray image display device M2 and transfers data therebetween via the communication cable. Only if data can be transferred, wireless communication may be adopted.

The X-ray imaging apparatus body M1 comprises the supporting part 30 supporting the X-ray generation part 10 and the X-ray detection part 20 which are opposed to each other, a driving part 60 for driving the supporting part 30, and an imaging apparatus body control part 70. The imaging apparatus body control part 70 is provided with the display part 88a and the operation part 86a. The operation part 86a may be also used to specify the positions or the like of living organs (imaging regions) which are symmetrically located with respect to a predetermined plane.

The X-ray generation part 10 is constituted of an X-ray source, i.e., an X-ray generator 11, formed of an X-ray tube for emitting an X-ray and the like and a radiation field control part 12 formed of a slit, a collimator, and the like for limiting the spread of X-ray beams B. The X-ray detection part 20 is formed of a cassette 22 provided with an X-ray detector 21 serving as an X-ray detection part to detect the X-ray emitted from the X-ray generator 11 and comprising MOS sensors, CCD sensors, or the like which two-dimensionally spread out. The cassette 22 is detachable/attachable from/to the X-ray detection part 20, and the X-ray detector 21 may be fixed to the X-ray detection part 20 without the cassette 22 interposed therebetween. The driving part 60 comprises the X-axis motor 60x and the Y-axis motor 60y which work together to horizontally move the rotation axis 30c of the supporting part 30, a Z-axis motor 60z for moving the supporting part 30 in the direction of the rotation axis 30c, and the rotation motor 60r for rotating the supporting part 30. The rotation motor 60r may rotate the axis 32 fixed to the supporting part 30 or the rotation motor 60r may rotate the supporting part 30 in a structure wherein the supporting part 30 is rotatable about the axis 32 only if driving is made so that the supporting part can be rotated about the rotation axis 30c.

Similarly, the X-axis motor 60x and the Y-axis motor 60y may move the axis 32 horizontally with respect to the above-described up-and-down moving frame 91, or the X-axis motor 60x and the Y-axis motor 60y may move the supporting part 30 horizontally with respect to the axis 32 in a structure wherein the supporting part 30 is displaceable horizontally with respect to the axis 32. The rotation motor 60r, the X-axis motor 60x, and the Y-axis motor 60y constitute the driving part 60 serving as a driving source for moving the supporting part 30 relatively with respect to the subject o. The imaging apparatus body control part 70 is formed of a CPU 71 for executing various control programs including a control program used for controlling the driving part 60 and comprises an X-ray generation part control part 72 for controlling the X-ray generation part 10 and an X-ray detection part control part 73 for controlling the X-ray detection part 20. The control part 70 of the X-ray imaging apparatus body M1 and a CPU 81 which is a constituent element of a control part of the X-ray image display device M2 collectively constitute a control part 70a. The operation panel 86a comprising a plurality of operation buttons and the like. As an input part used as a substitute for the operation panel 86a or used together with the operation panel 86a, an input part such as a keyboard, a mouse, a touch pen, or the like may be used besides the operation buttons. There may be a configuration wherein a voice command is received through a microphone and recognized. In other words, the operation panel 86a is an example of the operation part 86, and any element can be used as the operation part 86 only if it can receive the operation of an operator. The display part 88a is a display such as a liquid crystal monitor or the like.

For example, there may be a case where information such as characters or images required for the operation of the X-ray imaging apparatus body M1 is displayed on the display part 88a, or there may be another case where the X-ray imaging apparatus body M1 is connected to the X-ray image display device M2 described later and the content displayed on the display part 88b of the X-ray image display device M2 is also displayed on the display part 88a. There may still another case where various commands can be given to the X-ray imaging apparatus body M1 through a pointer operation or the like with a mouse or the like on characters or images displayed on the display part 88a. The subject holding part 40 and the driving part 60 serve as a moving part 65 for relatively moving the X-ray generator 11 and the X-ray detector 21 with respect to the subject o.

The X-ray imaging apparatus body M1 of the first preferred embodiment performs CT imaging of the subject o including imaging regions r (living organs symmetrically located with respect to a predetermined plane) in accordance with the command from the operation panel 86a or the X-ray image display device M2. The X-ray imaging apparatus body M1 receives various commands, coordinate data, or the like from the X-ray image display device M2 and sends the data of captured CT image to the X-ray image display device M2.

The X-ray image display device M2 has a configuration wherein the display part 88b and the operation part 86b are connected to the display device body 80. The display device body 80 comprises the CPU 81 for executing various programs, a storage part 82 formed of a hard disk and the like for storing various imaging data, images, or the like, an imaging region specifying part 83 for calculating the coordinates of a region specified by the operation part 86 and specifying the region as the imaging region r, and an image operation part 84 for reconstructing CT images and performing other calculations. The storage part 82, the imaging region specifying part 83, and the image operation part 84 constitute an image processing part 85.

The storage part 82 can store respective CT images of living organs, which are obtained by reconstructing only the imaging regions r from the data obtained by CT imaging, while associating the CT images with each other. The operation panel 86a and the operation part 86b constitute the operation part 86, and the operation part 86 specifies the imaging region r. Specifically, the operator uses the operation part 86 to specify a region to be captured in the screen (an illustration, a panoramic image, or the like) displaying part of or the whole of a living body, to thereby specify the imaging region r. In specification of the imaging region r by using the operation part 86, there may be a case where one of the living organs symmetrically located with respect to a predetermined plane is specified and the position of the other living organ is automatically obtained by the imaging region specifying part 83 or the like, or there may be another case where the operator specifies the positions of both the living organs. There may be still another case where without the operator's specification on the positions of the living organs, the operation part 86 specifies only information, an imaging target portion, or the like on the subject o and the imaging region specifying part 83 or the like automatically specifies the imaging region r. The display part 88a and the display part 88b constitute the display part 88. The imaging region r may be specified by giving an operation of the operation part 86 onto an image displayed on the screen of the display part 88 or the portion may be specified directly by using the operation part 86 to input the name of the portion or the code thereof without displaying any image for region specification on the screen.

Examples of automatic specification of imaging regions r include a case where performing specification of an imaging mode for the first living organ and the second living organ, such as the temporomandibular joint imaging mode, and CT imaging also achieves specification of the imaging region r as discussed later with reference to Step S5 of FIG. 14, and such a case is an example of the imaging region specifying part 83.

In such a case, by additionally performing selection of size group of the living body, such as selection of whether adult or child or of sex, serial imaging may be automatically performed in accordance with the size more finely. Specifically, the imaging region specifying part 83 may have a configuration wherein the operator manually specifies a specific position or another configuration wherein the operator only selects the mode or the size group of the living body and a specific position can be thereby automatically specified.

Figure 7:
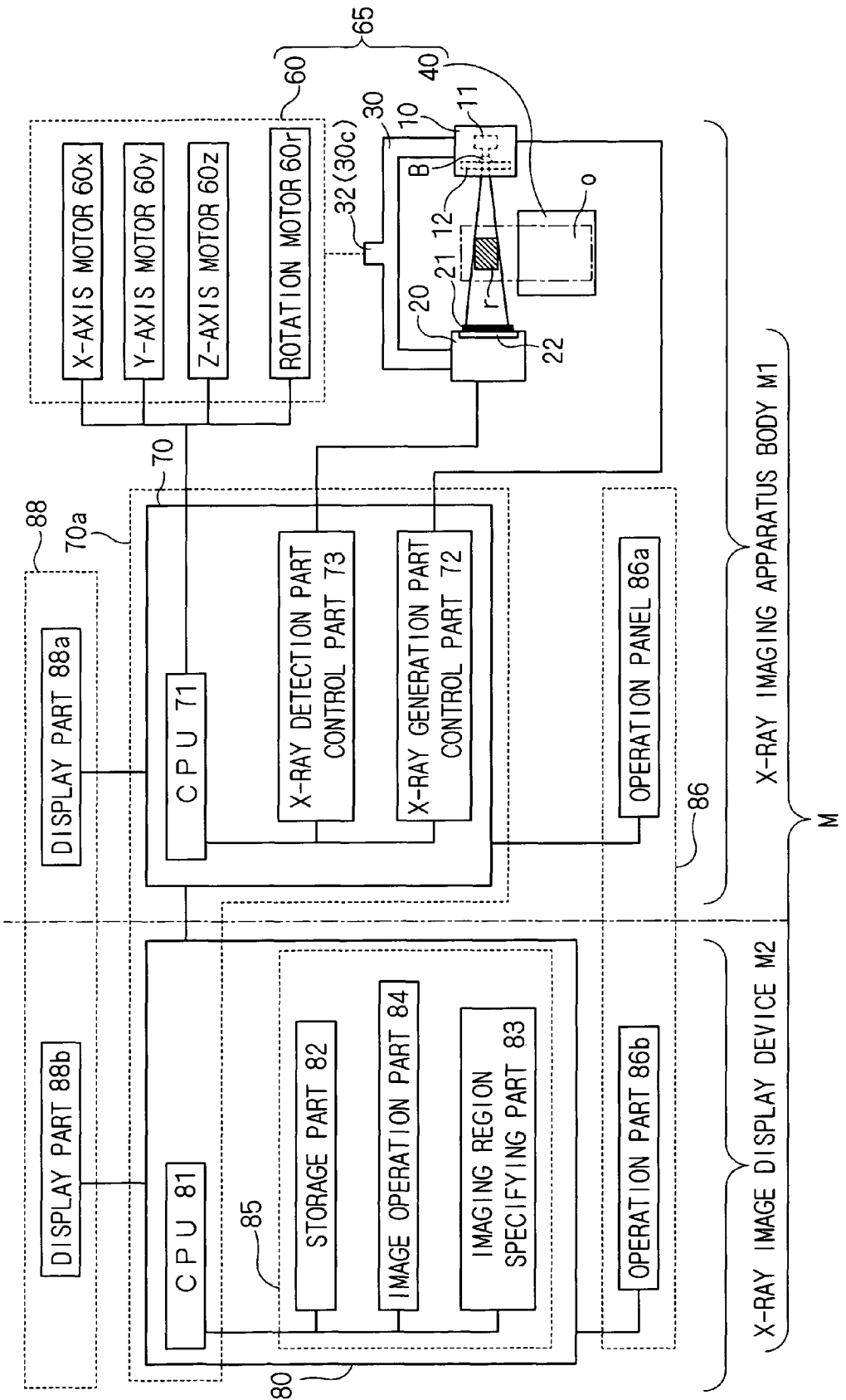
FIGS. 7 to 9 are block diagrams showing the medical X-ray CT imaging apparatus M in accordance with the first preferred embodiment of the present invention.
Figure 8:
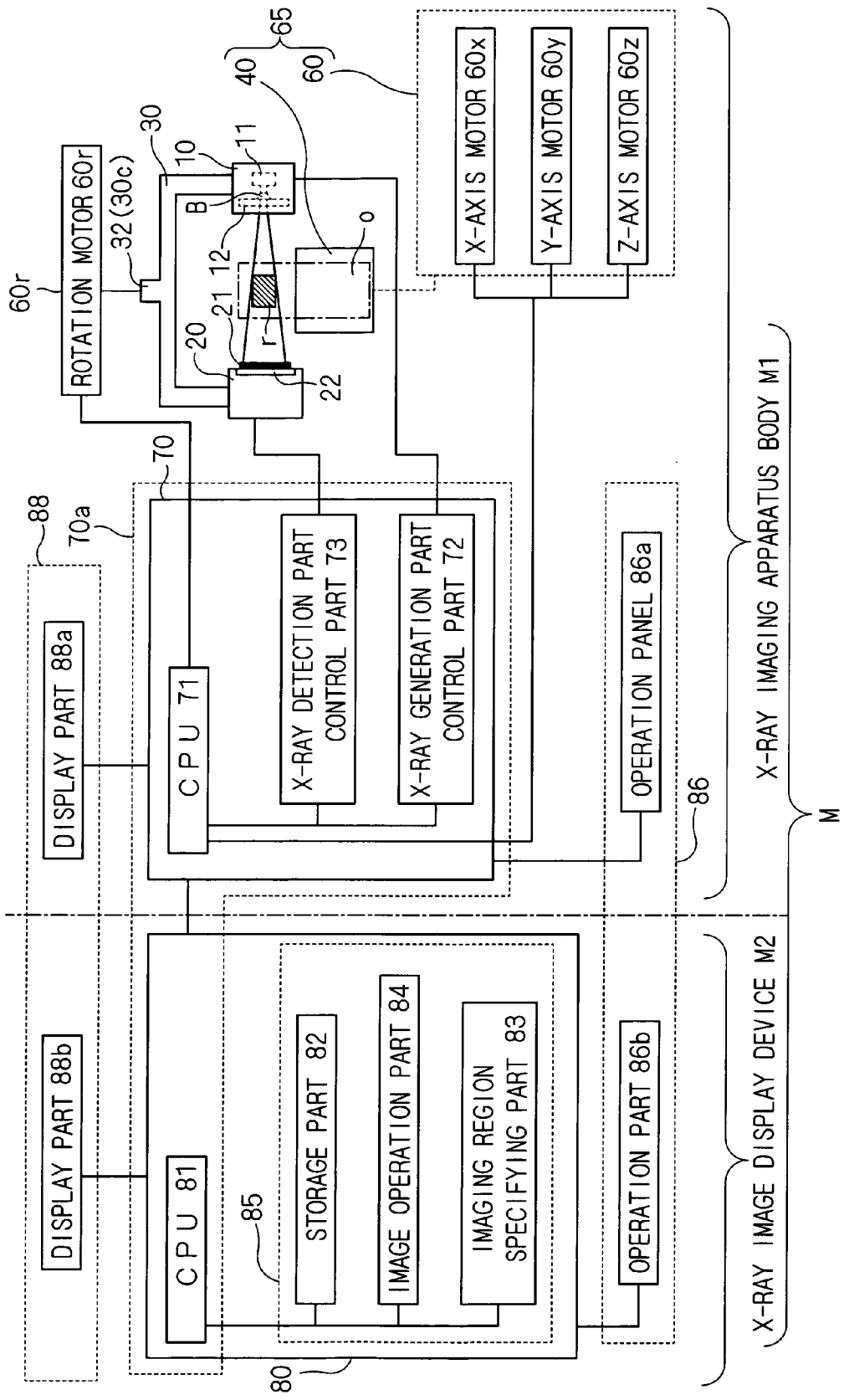

FIG. 8 is a block diagram showing a medical X-ray CT imaging apparatus M different from the medical X-ray CT imaging apparatus M shown in FIG. 7. The medical X-ray CT imaging apparatus M of FIG. 8 has the same basic configuration as that of the medical X-ray CT imaging apparatus M of FIG. 7 but is different from the medical X-ray CT imaging apparatus M of FIG. 7 in that the X-ray imaging apparatus body M1 of FIG. 8 comprises the rotation motor 60r for rotating the supporting part 30 but does not comprise the X-axis motor 60x and the Y-axis motor 60y for moving the axis 32 nor the Z-axis motor 60z for moving the supporting part 30 in the direction of the rotation axis 30c. The medical X-ray CT imaging apparatus M of FIG. 8 is different from the medical X-ray CT imaging apparatus M of FIG. 7 further in that the X-ray imaging apparatus body M1 of FIG. 8 comprises an X-axis motor 60x and a Y-axis motor 60y both for horizontally moving the subject o held by the subject holding part 40 and a Z-axis motor 60z for moving the subject holding part 40 up and down.

Figure 9:
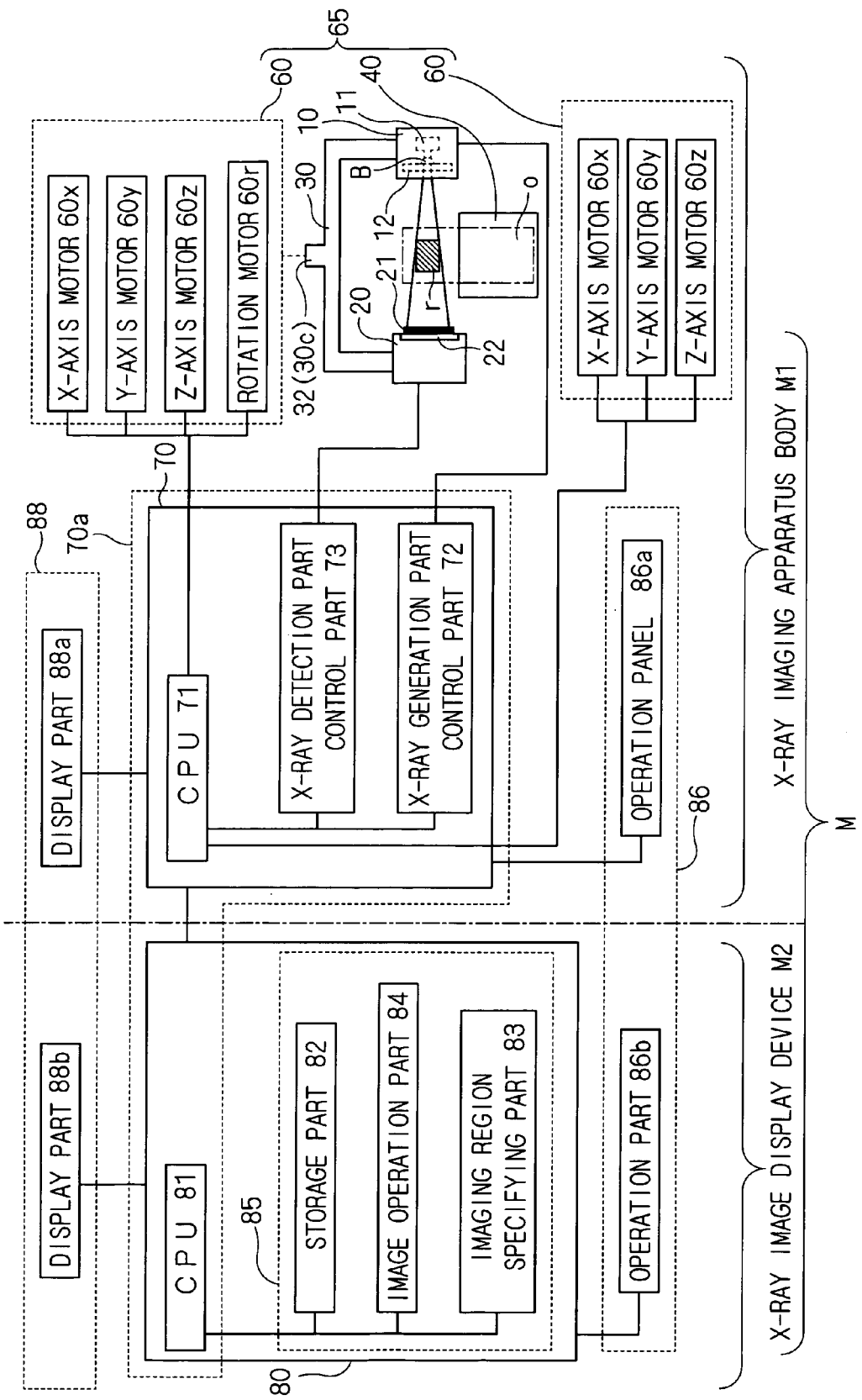

Further, FIG. 9 is a block diagram showing a medical X-ray CT imaging apparatus M different from the medical X-ray CT imaging apparatus M shown in FIG. 7. The medical X-ray CT imaging apparatus M of FIG. 9 has the same basic configuration as that of the medical X-ray CT imaging apparatus M of FIG. 7 but is different from the medical X-ray CT imaging apparatus M of FIG. 7 in that the X-ray imaging apparatus body M1 of FIG. 9 comprises another X-axis motor 60x and another Y-axis motor 60y which cooperate to horizontally move the subject holding part 40 and another Z-axis motor 60z for moving the subject holding part 40 up and down as well as the X-axis motor 60x and the Y-axis motor 60y which cooperate to horizontally move the axis 32, the Z-axis motor 60z for moving the supporting part 30 in the direction of the rotation axis 30c, and the rotation motor 60r for rotating the supporting part 30 in order to relatively move the subject o held by the subject holding part 40 with respect to the supporting part 30. In FIGS. 7 to 9, the X-axis motor 60x, the Y-axis motor 60y, and the Z-axis motor 60z serve as an axis moving part to relatively move the axis 32 with respect to the subject o, and the rotation motor 60r serves as a rotation driving part to drive the supporting part 30 and the subject holding part 40 to rotate relative to each other. If the subject holding part 40 is rotated, however, the living body may possibly faint, and therefore, in most cases, a configuration wherein the supporting part 30 is rotated without rotating the subject holding part is adopted.

Thus, there are various possible mechanisms of the driving part 60 and the moving part 65 to relatively move the supporting part 30 with respect to the subject o. There may be a configuration wherein part of the X-axis motor 60x, the Y-axis motor 60y, and the Z-axis motor 60z is provided on the drive side of the supporting part 30 and the rest of those is provided on the drive side of the subject holding part 40, or there may be another configuration wherein at least part of the X-axis motor 60x, the Y-axis motor 60y, and the Z-axis motor 60z is provided on both the drive sides. The latter case has the advantage that it is possible to increase the amount of relative movement or increase the variety of movement patterns since the amounts of movement on both sides can be integrated. In terms of cost, however, the former configuration is preferable, wherein part of the X-axis motor 60x, the Y-axis motor 60y, and the Z-axis motor 60z is provided on the drive side of the supporting part 30 and the rest of those is provided on the drive side of the subject holding part 40 as shown in FIGS. 7 and 8.

More specifically, including the above exemplary configurations, first to sixth exemplary configurations described below can be adopted. The following first to sixth exemplary configurations can be applied to an x-ray imaging apparatus having such a configuration like the X-ray imaging apparatus body M1 as shown in FIG. 2.

In the first exemplary configuration, the X-axis motor 60x and the Y-axis motor 60y both for horizontally moving the axis 32, the rotation motor 60r for rotating the supporting part 30, and the Z-axis motor 60z for moving the supporting part 30 up and down are provided in the up-and-down moving frame 91 and no driving part for moving the subject holding part 40 is provided at the bottom of the fixed frame 90.

In the second exemplary configuration, the X-axis motor 60x and the Y-axis motor 60y both for horizontally moving the axis 32, and the rotation motor 60r for rotating the supporting part 30 are provided in the up-and-down moving frame 91 and the Z-axis motor 60z for moving the subject holding part 40 up and down is provided at the bottom of the fixed frame 90.

In the third exemplary configuration, the rotation motor 60r for rotating the supporting part 30 is provided in the up-and-down moving frame 91 and the X-axis motor 60x and the Y-axis motor 60y both for horizontally moving the subject holding part 40 and the Z-axis motor 60z for moving the subject holding part 40 up and down are provided at the bottom of the fixed frame 90.

In the fourth exemplary configuration, the rotation motor 60r for rotating the supporting part 30 and the Z-axis motor 60z for moving the supporting part 30 up and down are provided in the up-and-down moving frame 91 and the X-axis motor 60x and the Y-axis motor 60y both for horizontally moving the subject holding part 40 are provided at the bottom of the fixed frame 90.

In the fifth exemplary configuration, the rotation motor 60r for rotating the supporting part 30 and the Z-axis motor 60z for moving the supporting part 30 up and down are provided in the up-and-down moving frame 91, one of the X-axis motor 60x and the Y-axis motor 60y is provided in the up-and-down moving frame 91 to move the rotation axis 30c of the supporting part 30, and the other is provided at the bottom of the fixed frame 90 to move the subject holding part 40. Thus, the total motion of the X-axis motor 60x and the Y-axis motor 60y causes the X-ray generator 11 and the X-ray detector 21 to horizontally move with respect to the subject o.

In the sixth exemplary configuration, the rotation motor 60r for rotating the supporting part 30 is provided in the up-and-down moving frame 91, the Z-axis motor 60z for moving the subject holding part 40 up and down is provided at the bottom of the fixed frame 90, one of the X-axis motor 60x and the Y-axis motor 60y is provided in the up-and-down moving frame 91 to move the axis 32, and the other is provided at the bottom of the fixed frame 90 to move the subject holding part 40. Thus, the total motion of the X-axis motor 60x and the Y-axis motor 60y causes the X-ray generator 11 and the X-ray detector 21 to horizontally move with respect to the subject o.

The relative movement described in the present invention refers to a movement, like the relation between the subject o and the supporting part 30 shown in FIGS. 7 to 9 and the above-discussed first to sixth exemplary configurations, wherein as viewed from one α of these, the other β is seen to be moving, whether the one α is actually still or moving. Specifically, as viewed from the subject o, the supporting part 30 is moving. This includes a case where the subject o is still and the supporting part 30 is moving, another case where the subject o is moving and the supporting part 30 is still, and still another case where both the subject o and the supporting part 30 are moving.

As the relative movement, there are various exemplary configurations other than those described above. The axis center of the axis 32 does not necessarily coincide with the center of rotation of an X-ray beam in imaging. The X-ray beam rotates, following the rotation of the supporting part 30, while being emitted. By combining the rotation of the supporting part 30 and the displacement of the axis 32, the center of rotation of the X-ray beam in imaging can be set at a portion different from the axis center of the axis 32.

Japanese Patent Application Laid Open Gazette No. 2007-29168 applied by the present applicant discloses an exemplary configuration wherein the center of rotation of the X-ray beam in imaging is thus set, and also in the present invention, CT imaging can be performed in such a manner.

In the first preferred embodiment, by using the medical X-ray CT imaging apparatus M having the above-described configuration, the imaging regions r of living organs (for example, bilaterally symmetrical temporomandibular joints or an upper tooth row and a lower tooth row which are vertically symmetrical) which are symmetrically located with respect to a predetermined plane are specified by the operation part 86 and the like and CT images of the specified imaging regions r are reconstructed from data obtained by CT imaging of the subject o including the living organs. Hereinafter, discussion will be made on a specific case where CT imaging is performed on temporomandibular joints. One of the living organs symmetrically located is defined as a first living organ and the other is defined as a second living organ.

Figure 10:
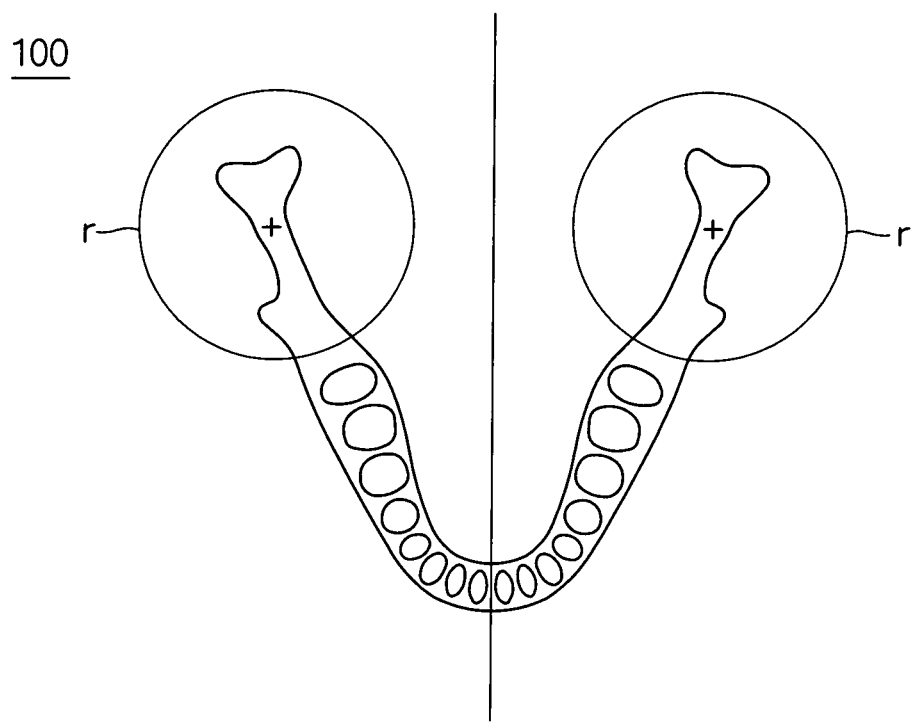
FIG. 10 is an illustration of a dental arch displayed by the medical X-ray CT imaging apparatus M in accordance with the first preferred embodiment of the present invention.

First, such an illustration 100 of a dental arch as shown in FIG. 10 or a volume rendering image of the dental arch which is reconstructed from the data obtained by the CT imaging of the subject o is displayed on the display part 88. The illustration or the like to be displayed is not limited to such a two-dimensional one as shown in FIG. 10 but may be a three-dimensional one. As an exemplary three-dimensional display, as seen in so-called computer graphics, three-dimensional image data of a stereoscopic dental arch of upper and lower teeth is generated and for example, the data is perspectively displayed or rotationally displayed by an additional operation. Observing the display part 88 on which the dental arch is displayed as shown in FIG. 10, the operator specifies the positions of the temporomandibular joints by using the operation part 86 to determine the positions as the imaging regions r. As to the specification of the positions of the temporomandibular joints, there may be a manner where the position of either one (for example, the right temporomandibular joint) is specified and the position of the other is automatically calculated, or the positions of both temporomandibular joints may be specified. Though the imaging regions r are represented by circles on the illustration 100 in FIG. 10, other representations may be adopted, for example, where the center of the imaging region r is represented by a cross, or the like. In the case where the illustration is three-dimensional, the imaging region r is three-dimensionally represented by a translucent sphere, a cylinder, or the like.

The image for region specification which is displayed on the display part 88 may be an image wherein the subject is illustrated, like the illustration 100 of the dental arch shown in FIG. 10, or an image obtained by actually imaging the subject with a camera for capturing normal visible light, instead of the illustration, only if the position has been set appropriately.

Figure 11:
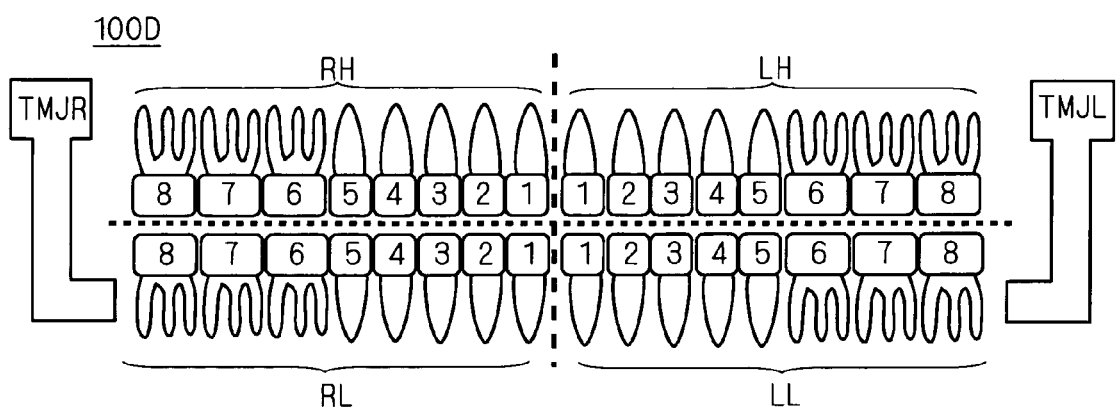
FIGS. 11 and 12 are views showing an exemplary image for region specification.

An actual shape is not necessarily required to be displayed and such an image like a schematic illustration 100D as shown in FIG. 11 may be displayed.

In FIG. 11, a series of teeth on the right side of the upper jaw, ranging from the front tooth to the molar, is defined as an RH group including the first to eighth teeth, and a series of teeth on the left side of the upper jaw, ranging from the front tooth to the molar, is defined as an LH group including the first to eighth teeth. A series of teeth on the right side of the lower jaw, ranging from the front tooth to the molar, is defined as an RL group including the first to eighth teeth, and a series of teeth on the left side of the lower jaw, ranging from the front tooth to the molar, is defined as an LL group including the first to eighth teeth. "TMJR" represents a right-side temporomandibular joint and "TMJL" represents a left-side temporomandibular joint.

The RL group and the LL group are symmetrical to the RH group and the LH group with respect to the occlusal surface, and the LH group and the LL group are symmetrical to the RH group and the RL group with respect to a plane including the median line. TMJR and TMJL are symmetrical to each other with respect to the plane including the median line. Herein, "the plane including the median line" refers to a plane for symmetrically dividing a head into left and right sides or a plane for symmetrically dividing a whole body into left and right sides. The "symmetrical relation with respect to the occlusal surface" and the "symmetrical relation with respect to the plane including the median line" are examples of "symmetry" in the present invention.

"The first living organ" and "the second living organ" of the present invention may be any portions only if these living organs are located symmetrically to each other, and are not limited to those symmetrical with respect to a body axis.

For specifying a portion, there may be a configuration, for example, wherein a touch panel is used as the display part 88 and the portion is specified by touching the touch panel. There may be another configuration which is well known in the field of computer, wherein the portion is specified by using a mouse or the like to move a pointer displayed on the screen of the display part 88, or still another configuration wherein the portion is specified by using a keyboard to input the number displayed in the image, such as "RH8" in the case where the first tooth on the upper right is intended to be specified.

In such a case, when the left and right portions are defined as a pair of the first living organ and the second living organ, there may be a manner where when the eighth tooth in the RH group is specified, for example, the eighth tooth in the LH group is also automatically specified. When the upper and lower portions are defined as a pair of the first living organ and the second living organ, there may be a manner where when the eighth tooth in the RH group is specified, for example, the eighth tooth in the RL group is also automatically specified.

Thus, in the case of left and right symmetrical pair, for example, when the eighth tooth in the RH group and the eighth tooth in the LH group are specified, CT imaging is performed consecutively on the portion corresponding to the eighth tooth in the RH group and the portion corresponding to the eighth tooth in the LH group.

In the case of upper and lower symmetrical pair, when the eighth tooth in the RH group and the eighth tooth in the RL group are specified, CT imaging is performed consecutively on the portion corresponding to the eighth tooth in the RH group and the portion corresponding to the eighth tooth in the RL group.

Further, not only the specification of a specific one tooth but also a range specification may be made. In the case where a touch panel is used as the display part 88, for example, by moving a finger to touch a range from one tooth to another tooth, such a control is made as to capture the image of the teeth in this range by CT imaging. In such a case, when the left and right portions are defined as a pair of the first living organ and the second living organ, there may be a manner where when a range from the sixth tooth to the eighth tooth in the RH group are specified, for example, a range from the sixth tooth to the eighth tooth in the LH group are also automatically specified. When the upper and lower portions are defined as a pair of the first living organ and the second living organ, there may be a manner where when a range from the sixth tooth to the eighth tooth in the RH group are specified, for example, a range from the sixth tooth to the eighth tooth in the RL group are also automatically specified.

Figure 12:
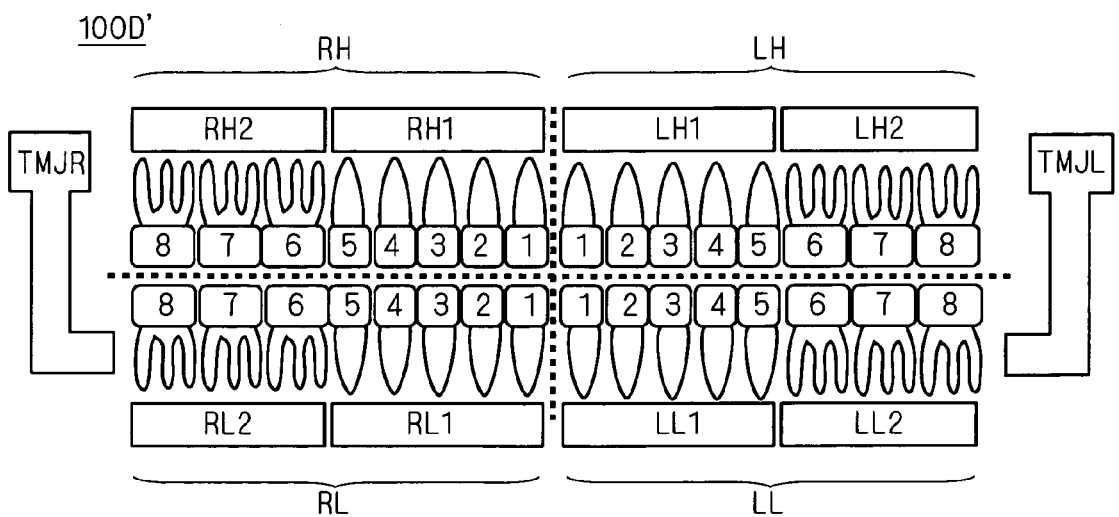

As to the range specification, as shown in FIG. 12, for example, there may be a manner where the whole is sectioned by zones to perform a zone specification. In the illustrated case, in a schematic image like the illustration 100D' similar to the illustration 100D of FIG. 11, zone sectioning is made where the zone near the front tooth, including the first to fifth teeth in the RH group, is represented as RH1 and the zone of the molars, including the sixth to eighth teeth in the RH group, is represented as RH2. Similarly, the zone near the front tooth, including the first to fifth teeth in the LH group, is represented as LH1 and the zone of the molars, including the sixth to eighth teeth in the LH group, is represented as LH2. The zone near the front tooth, including the first to fifth teeth in the RL group, is represented as RL1 and the zone of the molars, including the sixth to eighth teeth in the RL group, is represented as RL2. The zone near the front tooth, including the first to fifth teeth in the LL group, is represented as LL1 and the zone of the molars, including the sixth to eighth teeth in the LL group, is represented as LL2.

In the case where a touch panel is used as the display part 88, for example, when a frame represented by "RH2" shown in FIG. 12 is touched, the range containing the sixth to eighth teeth in the zone RH2 is specified to be captured by CT imaging.

In such a case, when the left and right portions are defined as a pair of the first living organ and the second living organ, there may be a manner where when the zone RH2 is specified, for example, the zone LH2 is also automatically specified. When the upper and lower portions are defined as a pair of the first living organ and the second living organ, there may be a manner where when the zone RH2 is specified, for example, the zone RL2 is also automatically specified.

Thus, in the case of left and right symmetrical pair, for example, when the sixth to eighth teeth in the RH group and the sixth to eighth teeth in the LH group are specified, CT imaging is performed consecutively on the portion corresponding to the sixth to eighth teeth in the RH group and the portion corresponding to the sixth to eighth teeth in the LH group.

In the case of upper and lower symmetrical pair, when the sixth to eighth teeth in the RH group and the sixth to eighth teeth in the RL group are specified, CT imaging is performed consecutively on the portion corresponding to the sixth to eighth tooth in the RH group and the portion corresponding to the sixth to eighth tooth in the RL group.

The RH group, the LH group, the RL group, or the LL group may be simply specified. As such an example, in the case where a touch panel is used as the display part 88, when a frame represented by "RH" shown in FIGS. 11 and 12 is touched, the range containing all the first to eighth teeth in the RH group is specified to be captured by CT imaging. In such a case, when the left and right portions are defined as a pair of the first living organ and the second living organ, there may be a manner where when the RH group is specified, the LH group is also automatically specified. When the upper and lower portions are defined as a pair of the first living organ and the second living organ, there may be a manner where when the RH group is specified, the RL group is also automatically specified.

Thus, in the case of left and right symmetrical pair, for example, when the RH group and the LH group are specified, CT imaging is performed consecutively on the portion corresponding to the RH group and the portion corresponding to the LH group.

In the case of upper and lower symmetrical pair, for example, when the RH group and the RL group are specified, CT imaging is performed consecutively on the portion corresponding to the RH group and the portion corresponding to the RL group.

There may be a case where a frame is prepared in advance and a desired range is specified by moving the frame on the display part 88 so that the frame can contain the desired range.

As another example, an image obtained by radiography of the subject may be used as the image for region specification which is displayed on the display part 88.

Figure 13:
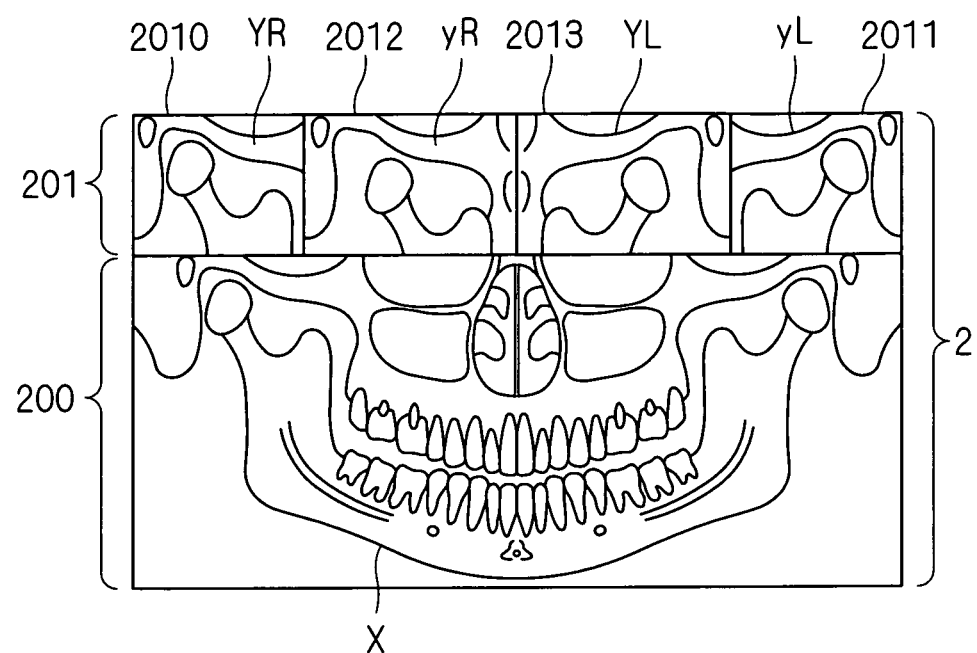
FIG. 13 is a view showing a display screen of the medical X-ray CT imaging apparatus M in accordance with the first preferred embodiment of the present invention.

Specifically, as discussed later, there may be a case where a panoramic image obtained by capturing the subject through panoramic radiography is displayed like a panoramic image 200 shown in FIG. 13 and used for specifying a position, or another case where transmitted images of the subject o are obtained from different angles prior to CT imaging, the transmitted image obtained from each angle is displayed, a target position is specified on the displayed transmitted image, and CT imaging is performed on the target portion.

Though the case where the schematic illustration is displayed has been discussed with reference to FIGS. 11 and 12, there may be a case where a plurality of buttons are provided in three-dimensional shape and arrangement of the illustration, to specify a position. This is an exemplary case for directly specifying the portion without displaying the image for region specification on the screen.

The above-discussed specifications by the tooth, by the range, by the sectioned group and the like can be applied to other preferred embodiments. For example, by overlapping an enclosing line representing the above zone on the illustration 100 in FIG. 10, or by displaying the enclosing line near the zone, the specification manners can be applied as appropriate.

After the imaging regions r are specified as shown in FIG. 10, the imaging region specifying part 83 or the like calculates the coordinates of each of the imaging regions r and the image operation part 84 reconstructs CT images of the imaging regions r from the CT imaging data of the subject o on the basis of the calculated coordinates.

In the CT imaging, while the supporting part 30 rotates about the rotation axis 30c, a frame image which is an X-ray transmitted image of each imaging region r for each very small rotation angle is acquired. From this frame image, three-dimensional X-ray absorption coefficient distribution data of the imaging region r is calculated. The CT image is reconstructed by performing back projection on the three-dimensional X-ray absorption coefficient distribution data. Specifically, until the display of the CT image, process steps of acquisition of the frame image, calculation of the three-dimensional X-ray absorption coefficient distribution data, and reconstruction of the CT image are executed. The image data of the frame image and the three-dimensional X-ray absorption coefficient distribution data are examples of the CT imaging data.

The CT images of the imaging regions r are displayed on the display part 88. FIG. 13 shows a display example of the screen displayed on the display part 88. In a display screen 2 shown in FIG. 13, the panoramic image 200 of a dental arch X including the temporomandibular joints and a CT cross sectional image 201 of the temporomandibular joints are displayed at an upper part and a lower part for comparison. The CT cross sectional image 201 includes an image 2010 showing a right-side temporomandibular joint YR in the closed state, an image 2011 showing a left-side temporomandibular joint YL in the closed state, an image 2012 showing a right-side temporomandibular joint yR in the open state, and an image 2013 showing a left-side temporomandibular joint yL in the open state. In order to obtain the CT images representing the temporomandibular joints YR and YL in the closed state and the temporomandibular joints yR and yL in the open state which are shown in FIG. 13, the above-discussed local CT imaging needs to be performed at least twice for the subject o in the closed state and the subject o in the open state.

Thus, in order to conduct a diagnosis on living organs symmetrically located with respect to a predetermined plane, it is preferable that these living organs should be displayed for comparison, and this conventionally requires a complicated operation wherein the operator positions one of the living organs and performs CT imaging thereon and after that, the operator positions the other and performs CT imaging thereon, and further needs to complete the images to be eventually displayed for comparison by displaying the reconstructed CT images and manually performing copy and paste of the CT images. The medical X-ray CT imaging apparatus M of the first preferred embodiment, however, specifies the imaging regions r of both the living organs and thereafter displays the images of the imaging regions r for comparison from the data obtained by the CT imaging of the subject o, and therefore the load of the operator can be reduced.

The medical X-ray CT image display device of the first preferred embodiment corresponds to the X-ray image display device M2. The CPU 81 performs various computations and other operations. The CPU 81 also acquires the CT images. In this meaning, the CPU 81 serves as the CT image acquisition part of the medical X-ray CT image display device of the first preferred embodiment. The CT images obtained by X-ray CT imaging, using a cone beam B, of the first living organ and the second living organ which are symmetrically located with respect to a predetermined plane may be acquired from the X-ray imaging apparatus body M1 or may be acquired from the storage part 82. A display part serving as the medical X-ray CT image display device of the first preferred embodiment corresponds to the display part 88b, which displays the CT image of the first living organ and the CT image of the second living organ both of which are acquired by the CT image acquisition part as shown in FIG. 13 on one display screen for comparison.

(The Second Preferred Embodiment)

A medical X-ray CT imaging apparatus M of the second preferred embodiment changes the imaging condition on the basis of whether the subject o is an adult or a child. With reference to the flowchart of FIG. 14, an operation of the medical X-ray CT imaging apparatus M of the second preferred embodiment will be discussed. The configuration of the medical X-ray CT imaging apparatus M of the second preferred embodiment is the same as that of the medical X-ray CT imaging apparatus M of the first preferred embodiment, and therefore detailed description thereof will be omitted.

Figure 14:
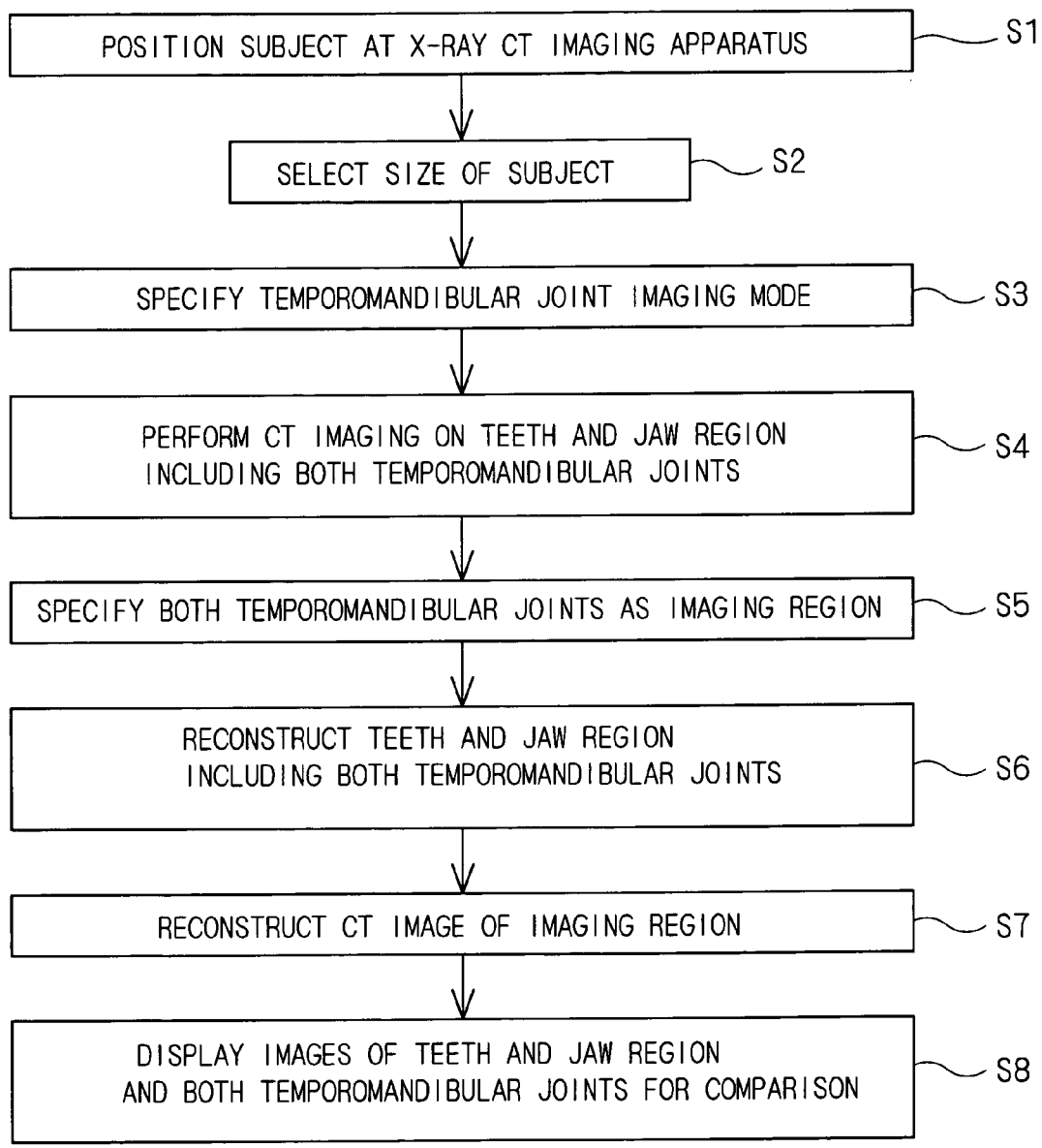
FIGS. 14 and 15 are flowcharts showing an operation of the medical X-ray CT imaging apparatus M in accordance with a second preferred embodiment of the present invention.

First, in Step S1 of FIG. 14, the subject o is positioned at the X-ray CT imaging apparatus. Specifically, in Step S1, the subject o is held by the subject holding part 40. In Step S2, the operation part 86 selects the size of the subject o, specifically, whether the subject o has the size of adult or the size of child. Further, In Step S2, imaging condition is set on the basis of the selected size of the subject o. The size of the living organ of an adult is different from that of the living organ of a child, and therefore it is desirable that the imaging is performed under the imaging condition for adult. Specifically, as the imaging condition to change the size of the imaging region r, the width of the slit of the radiation field control part 12 for controlling the range of the X-ray beam emitted from the X-ray source may be changed or the enlargement ratio may be changed by using the moving part to change the positional relation between the subject o and the X-ray generator 11. Since the enlargement ratio is usually represented by the ratio of the distance between the subject and the X-ray detector to the distance between the X-ray source and the X-ray detector, the ratio has only to be changed. By controlling the tube voltage, the tube current, the irradiation time, and the rotation speed, the X-ray radiation dose may be changed, for example, reduced for a child as compared with the case for an adult. The change in the width of the slit and the change in the enlargement ratio may be combined. The size of the imaging region r is changed not only depending on whether the subject is an adult or a child but also in accordance with the type of living organ to be imaged. For example, the size of the imaging region r is changed between when the imaging target is an auditory ossicle and when the imaging target is a cochlea. The size of the imaging region r is changed by an imaging region changing part constituted of the X-ray generation part control part 72 and the X-ray detection part control part 73.

Next, in Step S3, the operation part 86 specifies the temporomandibular joint imaging mode.

In Step S4, performed is CT imaging of the teeth and jaw region including both temporomandibular joints as the subject o. In Step S5, both temporomandibular joints are specified as the imaging regions r. As discussed in the first preferred embodiment, as the specification manner, one or both of the temporomandibular joints may be specified by the operation part 86 with the illustration thereof or the like or may be specified on the basis of data set in advance.

Next, in Step S6, the CT image of the teeth and jaw region including both temporomandibular joints is reconstructed. In Step S7, both the temporomandibular joints in the imaging regions r specified in Step S5 are reconstructed as CT images. Then, in Step S8, the CT image of the teeth and jaw region which is reconstructed in Step S6 and the CT images of both the temporomandibular joints which are reconstructed in Step S7 are displayed on the display part 88 (display device). On the display part 88, the CT images of the left and right temporomandibular joints are displayed for comparison. There may be a case where it is considered that the specification of the imaging region r in Step S5 is executed through the selection of the temporomandibular joint mode in Step S3 and the CT imaging in Step S4 and without particularly displaying the illustration, the process automatically goes to the reconstruction of the CT images of the temporomandibular joints in Step S7 and the display of the CT images of the temporomandibular joints in Step S8. If the subject to be imaged is a living body having normal and general physique and skeleton, the positions in the three-dimensional space where the X-ray imaging apparatus body M1 is provided, where one of the paired organs is located and the other is located, may be set in advance as coordinate data. Since the positions of the left and right temporomandibular joints can be set as coordinate data, it is possible to reconstruct the right temporomandibular joint region in the three-dimensional space which would be present if the subject has normal and general physique and skeleton. This allows the process to automatically go to the display of the CT images of the temporomandibular joints. In this case, the specification of the temporomandibular joint mode and execution of the CT imaging also serve as the specification of the imaging regions in Step S5.

Figure 15:
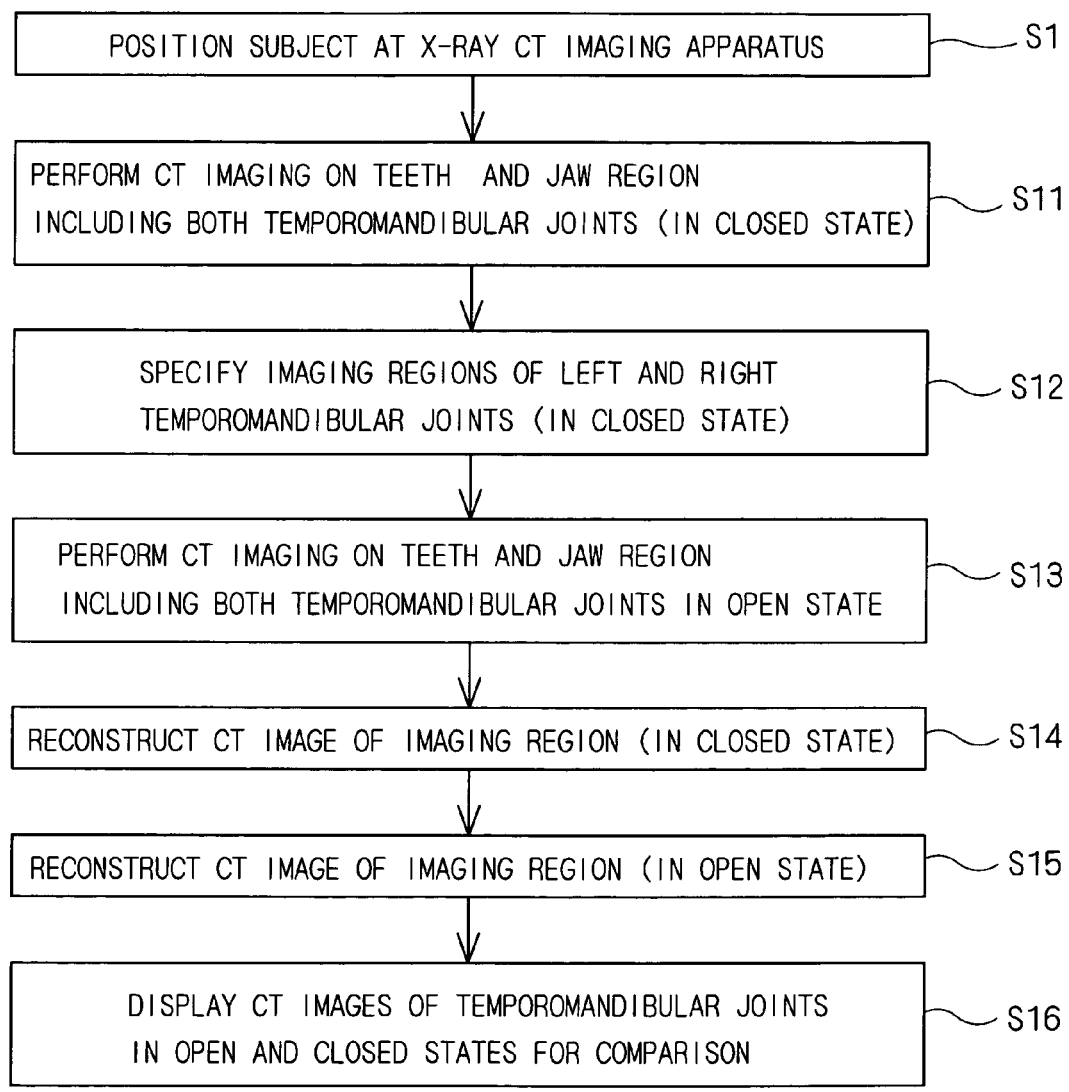

With reference to the flowchart of FIG. 14, the operation of the medical X-ray CT imaging apparatus M for performing the CT imaging on the temporomandibular joints in the open or closed state has been discussed. Now, with reference to the flowchart of FIG. 15, an operation of the medical X-ray CT imaging apparatus M for performing the CT imaging on the temporomandibular joints in the open and closed states will be discussed. In the flowchart of FIG. 15, after positioning the subject o at the X-ray CT imaging apparatus in Step S1, Steps S2 and S3 are executed like in FIG. 14 but Steps S2 and S3 are not shown.

First, in Step S11, performed is CT imaging of the teeth and jaw region including both the temporomandibular joints in the closed state as the subject o. In Step S12, both the temporomandibular joints in the closed state are specified as the imaging regions r. Further, in Step S13, performed is CT imaging of the teeth and jaw region including both the temporomandibular joints in the open state as the subject o. In Step S14, the CT images of the temporomandibular joints in the imaging regions r specified in Step S12 are reconstructed. In Step S15, on the basis of the positions of both the temporomandibular joints in the imaging regions r specified in Step S12, the CT images of both the temporomandibular joints in the open state (the imaging regions r) are reconstructed from the data obtained by the CT imaging in Step S13. In Step S16, the CT images of both the temporomandibular joints in the closed state which are reconstructed in Step S14 and the CT images of both the temporomandibular joints in the open state which are reconstructed in Step S15 are displayed on the display part 88 (display device) for comparison.

Now, discussion will be made on the coordinates operation on the specification in Step S5, the reconstruction in Step S7, and the display in Step S8. If the subject to be imaged is a living body having normal and general physique and skeleton, the positions in the three-dimensional space where the X-ray imaging apparatus body M1 is provided, where one of the paired organs is located and the other is located, may be set in advance as coordinate data. By utilizing this, a reconstruction calculation can be performed on the region and therearound on the basis of the coordinate data. For example, if a key for "right temporomandibular joint" is prepared, since it is possible to set an image processing wherein the reconstruction calculation is performed on the region of the right temporomandibular joint in the three-dimensional space which would be present if the subject has normal and general physique and skeleton only by turning the key ON without any input of specific three-dimensional coordinates by the operator, it is possible to reconstruct the CT image of the right temporomandibular joint by one-touch operation only if the subject o is reliably fixed to the subject holding part 40. Since similar calculation can be performed on the left temporomandibular joint, it is possible to reconstruct the CT images of one temporomandibular joint and the other temporomandibular joint only by specifying one temporomandibular joint. The same applies to other organs as well as the temporomandibular joints.

By making setting so that the region displayed in the illustration 100 should coincide with the position of the region in the three-dimensional space where the X-ray imaging apparatus body M1 is provided, it is possible to reconstruct the CT image of a desired region. Thus, the region specification on the illustration can be converted into the specification of the region in the three-dimensional space for the subject o fixed to the subject holding part 40. As a matter of course, instead of the data on the normal and general physique and skeleton, data on physiques and skeletons of individual living bodies may be prepared and used. As discussed earlier, without displaying any image for region specification, like the illustration 100 of FIG. 10, on the screen, the portion may be specified directly by using the operation part 86 to input the name of the portion or code thereof. This can be achieved on the basis of the above-discussed coordinate data. There may be a configuration, for example, wherein a key for starting execution of reconstruction of the CT images of the temporomandibular joints is set, such as a key of a keyboard or a key displayed on the screen to be clicked by a mouse, and the key is, turned ON. In the image processing, there may be a case where the coordinates in the three-dimensional space where the X-ray imaging apparatus body M1 is provided are determined and the coordinates are utilized for the display of the CT images. For example, the three-dimensional coordinates of an arbitrary position in the case where the subject o is fixed to the subject holding part 40, e.g., the position corresponding to the center of the head are determined as (0, 0, 0), and the respective coordinates of x, y, and z which are orthogonal to one another with the above point as the origin point can be used for calculation. If the position corresponding to the center of the head is determined as the origin point (0, 0, 0), for example, calculation is performed with the coordinates of the position after movement by 100 units from the origin point in the right direction of the patient determined as (−100, 0, 0) and the coordinates of the position after movement by 100 units from the origin point in the left direction of the patient determined as (100, 0, 0). By using such three-dimensional coordinates, for example, when a specific position of the center of the right or left caput mandibulae is specified, the coordinates of the specific position may be displayed. The distance between the specific position of the center of the right caput mandibulae and the specific position of the center of the left caput mandibulae may be measured. The angles which a straight line connecting arbitrary two points set for a portion makes with respect to the respective planes of xy, xz, and yz may be measured.

Figure 16:
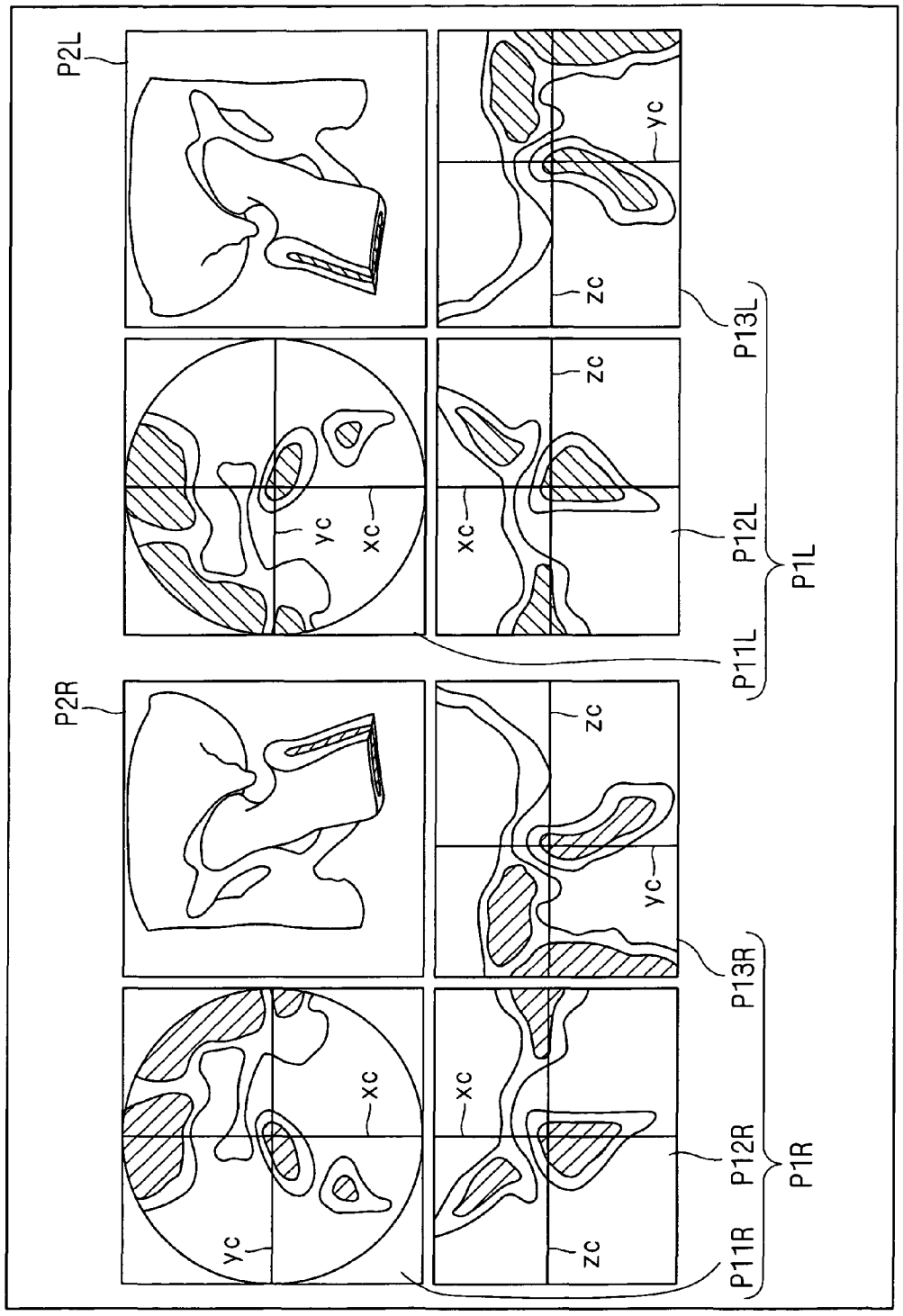
FIGS. 16 and 17 are views showing a display screen of the medical X-ray CT imaging apparatus M in accordance with the second preferred embodiment of the present invention.

FIG. 16 shows the CT images of the temporomandibular joints in the closed state which are displayed on the display part 88 in Step S8 of FIG. 14. In FIG. 16, however, only the CT images of the left and right temporomandibular joints are displayed for comparison but no CT image of the teeth and jaw region is displayed. In the CT images shown in FIG. 16, a cross sectional CT image P1R of the right-side temporomandibular joint of the subject o and a volume rendering image P2R of the right-side temporomandibular joint are displayed on the left side of the screen and a cross sectional CT image P1L of the left-side temporomandibular joint of the subject o and a volume rendering image P2L of the left-side temporomandibular joint are displayed on the right side of the screen. The cross sectional CT image P1R includes a cross sectional CT image P11R of the right-side temporomandibular joint sectioned by an xy plane which is shown in the upper left, a cross sectional CT image P12R of the right-side temporomandibular joint sectioned by an xz plane which is shown in the lower left, and a cross sectional CT image P13R of the right-side temporomandibular joint sectioned by a yz plane which is shown in the lower right. Similarly, the cross sectional CT image P1L includes a cross sectional CT image P11L of the left-side temporomandibular joint sectioned by the xy plane which is shown in the upper left, a cross sectional CT image P12L of the left-side temporomandibular joint sectioned by then xz plane which is shown in the lower left, and a cross sectional CT image P13L of the left-side temporomandibular joint sectioned by the yz plane which is shown in the lower right.

In the CT imaging, since the position of an imaging target portion, i.e., each temporomandibular joint in this case, can be detected, a default cross section displayed first in each of the cross sectional CT images can be set, for example, near the center of the portion. In the figure, the cross section of each cross sectional CT image is set centering the center of a caput mandibulae and therearound of each temporomandibular joint. As discussed below, the position of the cross section can be moved to a desired position by, for example, cursors zc, yc, and xc, or the like.

In the display example of FIG. 16, the line-of-sight directions are set so that the volume rendering image P2R of the right-side temporomandibular joint and the volume rendering image P2L of the left-side temporomandibular joint may be displayed in mirror symmetry with respect to a plane of the median line of the subject o. Similarly, in the display example of FIG. 17, as to the cross sectional CT image P11R and the cross sectional CT image P11L, the cross sectional CT image P12R and cross sectional CT image P12L, and the cross sectional CT image P13R and the cross sectional CT image P13L, the respective slice positions (slice planes) are positioned in mirror symmetry with respect to the plane of the median line of the subject o. There may be a layout where by changing the line-of-sight direction of one of the volume rendering images, the other volume rendering image is also changed so that the line-of-sight directions in mirror symmetry should be maintained. Similarly, there may be another layout where by changing the slice position of one of the cross sectional CT images, the slice position of the other cross sectional CT image is changed so that the positions in mirror symmetry should be maintained.

Though not shown in FIG. 16, cursors associated with the cross sectional CT images P1R and P1L may be set in the volume rendering images P2R and P2L of the temporomandibular joints. The cursors can be moved by using the operation part 86, and by moving the cursors, the cross sectional CT images P1R and P1L at the positions of the cursors can be displayed. More specifically, cross-sectional planes of X, Y, and Z which are orthogonal to one another are set with respect to the three-dimensional image data such as the volume rendering images P2R and P2L and the like of the temporomandibular joints, and the images of the cross-sectional planes are displayed like the cross sectional CT images P1R and P1L.

The positions of the cross-sectional planes are not be fixed but by using the operation part 86, the positions of the cross-sectional planes at desired depths can be set. In each image of the cross-sectional plane, the positions of the other cross-sectional planes are displayed with the cursors, and by moving the cursors, the images of the other cross-sectional planes become those of the cross-sectional planes specified by the movement of the cursors.

As to x, y, and z of such well-known three-dimensional coordinates as discussed above, x axis, y axis, and z axis are assumed. An X cross-sectional plane is a plane orthogonal to the x axis, a Y cross-sectional plane is a plane orthogonal to the y axis, and a Z cross-sectional plane is a plane orthogonal to the z axis.

If the two-dimensional plane consisting of y and z in an x coordinate is defined as the yz plane, the X cross-sectional plane uses the yz plane as the cross-sectional plane. If the two-dimensional plane consisting of x and z in a y coordinate is defined as the xz plane, the Y cross-sectional plane uses the xz plane as the cross-sectional plane. If the two-dimensional plane consisting of x and y in a z coordinate is defined as the xy plane, the Z cross-sectional plane uses the xy plane as the cross-sectional plane.

The x cursor xc indicating the position of the yz plane (X cross-sectional plane) is shown in the xz plane (Y cross-sectional plane) and the xy plane (Z cross-sectional plane). The y cursor yc indicating the position of the xz plane (Y cross-sectional plane) is shown in the yz plane (X cross-sectional plane) and the xy plane (Z cross-sectional plane). The z cursor zc indicating the position of the xy plane (Z cross-sectional plane) is shown in the yz plane (X cross-sectional plane) and the xz plane (Y cross-sectional plane). The cursors zc, yc, and xc are moved by an operation of a pointer with a mouse, to thereby move the respective positions of the yz plane (X cross-sectional plane), the xz plane (Y cross-sectional plane), and the xy plane (Z cross-sectional plane).

The x cursor xc in the xz plane (Y cross-sectional plane) and the x cursor xc in the xy plane (Z cross-sectional plane) are interlocked, and when one of the cursors is moved, the other is automatically moved. The y cursor yc in the yz plane (X cross-sectional plane) and the y cursor yc in the xy plane (Z cross-sectional plane) are in the same relation, and the z cursor zc in the yz plane (X cross-sectional plane) and the z cursor zc in the xz plane (Y cross-sectional plane) are also in the same relation.

Therefore, when the cursor indicating the Y cross-sectional plane displayed on the X cross-sectional plane image is moved, the cursor indicating the position of the Y cross-sectional plane displayed on the Z cross-sectional plane image is also moved interlockedly. The same relation applies to other cross-sectional plane images.

There may be a case where when an imaging region of any one of the first living organ and the second living organ is specified and an arbitrary cross sectional CT image is displayed, the corresponding cross sectional CT image of the imaging region of the other living organ located symmetrically to the above one with respect to the predetermined plane is also automatically displayed on the same display screen for comparison.

In FIG. 16, for example, setting is made so that when the x cursor xc shown in the cross sectional CT image P12R is moved leftward as one faces the figure by the amount α of movement, the x cursor xc shown in the cross sectional CT image P12L is automatically moved rightward by the amount α of movement, and the position of the yz plane (X cross-sectional plane) showing in the cross sectional CT image P13R and the position of the yz plane (X cross-sectional plane) showing in the cross sectional CT image P13L are also changed with the movement of the x cursor. In this case, the x cursor xc shown in the cross sectional CT image P11R and the x cursor xc shown in the cross sectional CT image P11L are also moved interlockedly.

In FIG. 16, setting is made so that when the z cursor zc shown in the cross sectional CT image P12R is moved downward as one faces the figure by the amount β of movement, the z cursor zc shown in the cross sectional CT image P12L is automatically moved downward by the amount β of movement, and the position of the xy plane (Z cross-sectional plane) showing in the cross sectional CT image P11R and the position of the xy plane (Z cross-sectional plane) showing in the cross sectional CT image P11L are also changed with the movement of the z cursor. In this case, the z cursor zc shown in the cross sectional CT image P13R and the z cursor zc shown in the cross sectional CT image P13L are also moved interlockedly.

Thus, setting may be made so that by moving a cursor in any one of the respective three cross-sectional plane images of the first living organ and the second living organ, the cursor of the three cross sections of the other living organ is moved symmetrically with respect to the predetermined plane, i.e., the section plane including the median line by which the living body is divided into left and right sides in the above case, and the cross sectional CT images corresponding to the positions of the moved cursors are displayed as to the first living organ and the second living organ.

Figure 17:
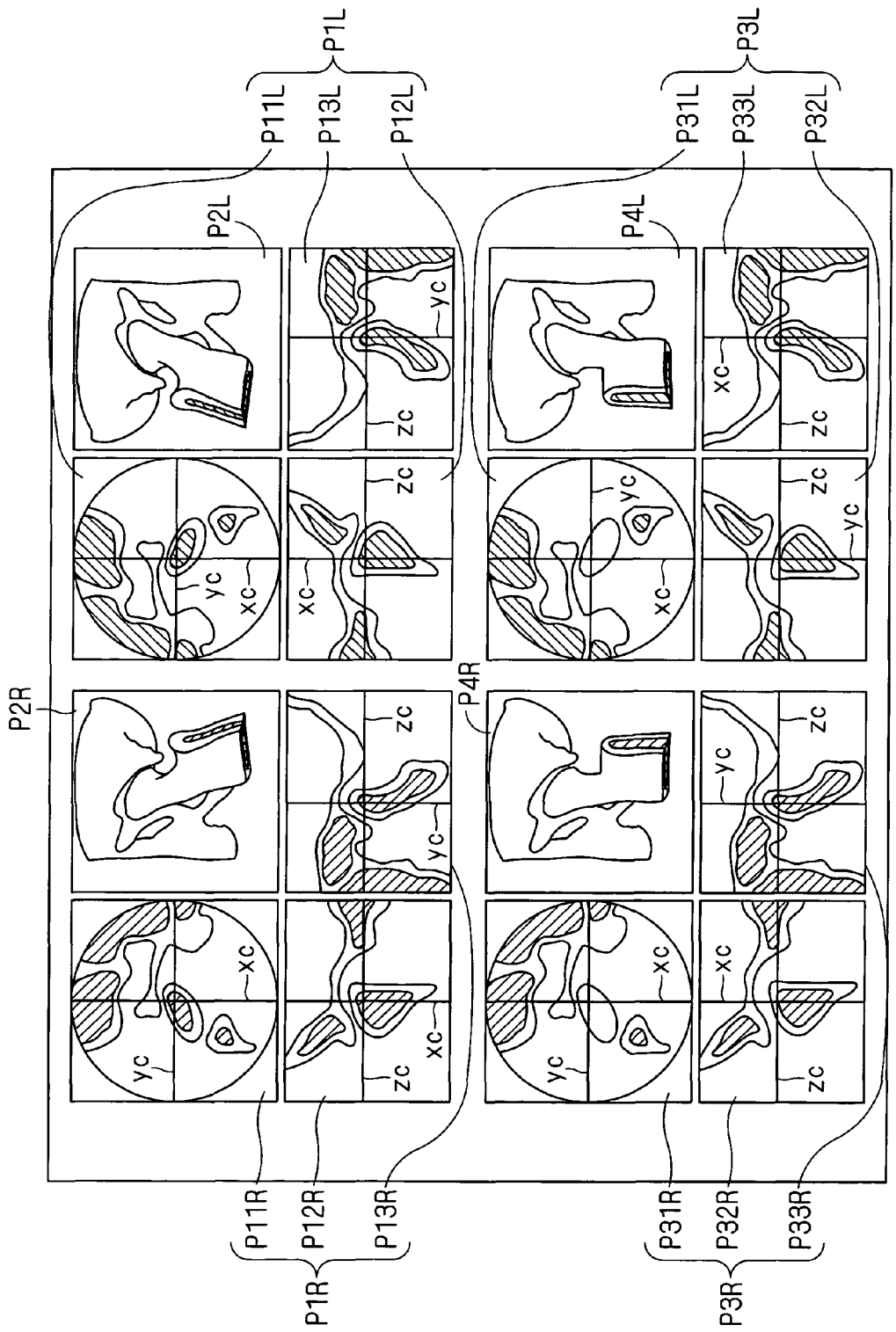

On the other hand, FIG. 17 shows the CT images of the temporomandibular joints in the closed and open states which are displayed on the display part 88 in Step S16 of FIG. 15. In the CT images shown in FIG. 17, the CT images of the closed state are displayed on the upper stage of the screen, and the CT images of the open state are displayed on the lower stage of the screen. The CT images on the upper stage of FIG. 17 are the same as the CT images shown in FIG. 16. The cross sectional CT image P1R of the right-side temporomandibular joint in the closed state and the volume rendering image P2R of the right-side temporomandibular joint are displayed on the left side of the screen. The cross sectional CT image P1L of the left-side temporomandibular joint in the closed state and the volume rendering image P2L of the left-side temporomandibular joint are displayed on the right side of the screen. In the CT images on the lower stage of FIG. 17, a cross sectional CT image P3R of the right-side temporomandibular joint in the open state and a volume rendering image P4R of the right-side temporomandibular joint are displayed on the left side of the screen, and a cross sectional CT image P3L of the left-side temporomandibular joint in the open state and a volume rendering image P4L of the left-side temporomandibular joint are displayed on the right side of the screen. The cross sectional CT image P3R includes a cross sectional CT image P31R of the right-side temporomandibular joint in the open state sectioned by the xy plane which is shown in the upper left, a cross sectional CT image P32R of the right-side temporomandibular joint in the open state sectioned by the xz plane which is shown in the lower left, and a cross sectional CT image P33R of the right-side temporomandibular joint in the open state sectioned by the yz plane which is shown in the lower right. Similarly, the cross sectional CT image P3L includes a cross sectional CT image P31L of the left-side temporomandibular joint in the open state sectioned by the xy plane which is shown in the upper left, a cross sectional CT image P32L of the left-side temporomandibular joint in the open state sectioned by the xz plane which is shown in the lower left, and a cross sectional CT image P33L of the left-side temporomandibular joint in the open state sectioned by the yz plane which is shown in the lower right.

Thus, since the medical X-ray CT imaging apparatus M of the second preferred embodiment performs the X-ray CT imaging of the temporomandibular joints in the open or closed state or the temporomandibular joints in the open and closed states while setting the adult size or the child size, it is possible to automatically control the X-ray radiation condition, such as the tube current and the tube voltage and the like, of an optimal X-ray power supply, and possible for the apparatus to automatically determine roughly the center positions of the imaging regions r which are the position of the living organs (on the basis of the factory setting value) only by selecting adult or child.

Further, the medical X-ray CT imaging apparatus M of the second preferred embodiment performs the CT imaging on the temporomandibular joints in the closed and open states and reconstructs CT images on the basis of the data captured through the CT imaging. The medical X-ray CT imaging apparatus M, however, performs the CT imaging on the temporomandibular joints in an intermediate state (between the closed and open states) at least once as well as the CT imaging on the temporomandibular joints in the closed and open states and reconstructs the CT images on the basis of the data captured through the CT imaging, to continuously reproduce the CT images. It is thereby possible to display the CT images of the temporomandibular joints from the open state to the closed state as moving images on the display part 88.

Though the above discussion has been made on the case where the CT imaging is consecutively performed on the first living organ and the second living organ such as the left and right temporomandibular joints, the CT imaging may be performed not only on the first living organ and the second living organ but also mixedly on another portion.

Such another portion is referred to as a third living organ, which will be described with reference to FIG. 18. Herein, the "third living organ" refers to a CT imaging target portion different from the first living organ and the second living organ and may be singular or plural.

Figure 18:
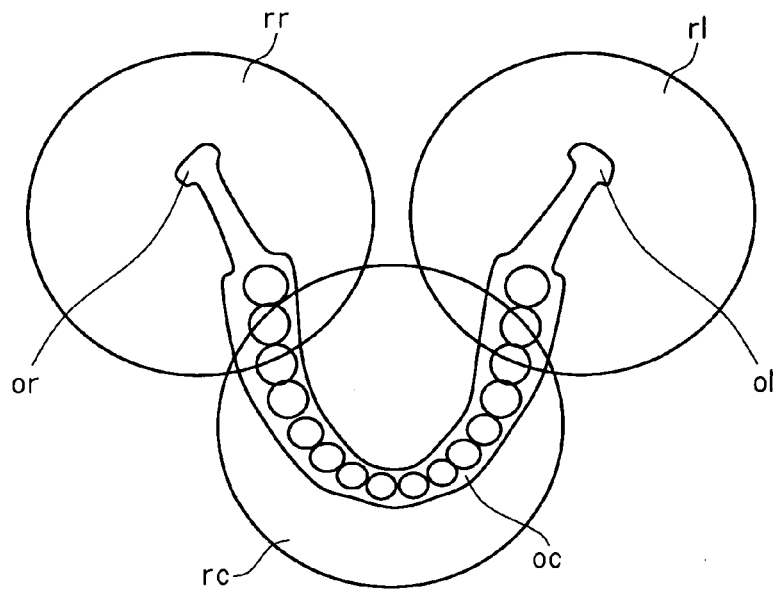
FIGS. 18 and 19 are views showing an exemplary case of setting an imaging region.

FIG. 18 shows an exemplary case where assuming that the right-side temporomandibular joint and portions in the vicinity thereof are defined as a right-side living organ or, the left-side temporomandibular joint and portions in the vicinity thereof are defined as a left-side living organ ol, and portions centering row of teeth between both the temporomandibular joints are defined as a central living organ oc, set are a right-side imaging region rr for the CT imaging of the right-side living organ or, a left-side imaging region rl for the CT imaging of the left-side living organ ol, and a central imaging region rc for the CT imaging of the central living organ oc. In this exemplary case, the third living organ is a portion located between the first living organ and the second living organ and continuous with the first and second living organs.

The CT imaging is performed consecutively on the imaging region rr, the imaging region rl, and the imaging region rc, but the sequence is not limited to this.

Examples of the sequence are shown below. In each of the following examples, the CT imaging is performed in the order of description.

Example 1: the CT imaging on the imaging region rr, the CT imaging on the imaging region rl, and the CT imaging on the imaging region rc, Example 2: the CT imaging on the imaging region rl, the CT imaging on the imaging region rr, and the CT imaging on the imaging region rc, Example 3: the CT imaging on the imaging region rc, the CT imaging on the imaging region rr, and the CT imaging on the imaging region rl, Example 4: the CT imaging on the imaging region rc, the CT imaging on the imaging region rl, and the CT imaging on the imaging region rr, Example 5: the CT imaging on the imaging region rr, the CT imaging on the imaging region rc, and the CT imaging on the imaging region rl, and Example 6: the CT imaging on the imaging region rl, the CT imaging on the imaging region rc, and the CT imaging on the imaging region rr.

Herein, it is assumed that one of the right-side living organ or and the left-side living organ of is the first living organ, the other is the second living organ, and the central living organ oc is the third living organ.

In Examples 1 and 2, the CT imaging on the third living organ is performed after the serial CT imaging on the first living organ and the second living organ.

In Examples 3 and 4, the CT imaging on the third living organ is performed before the serial CT imaging on the first living organ and the second living organ.

In Examples 5 and 6, the CT imaging on the third living organ is performed between the serial CT imaging on the first living organ and the second living organ.

The sizes of the imaging region rr, the imaging region rl, and the imaging region rc are set so that the total size of the imaging region rr, the imaging region rl, and the imaging region rc may contain the entire dental arch including all of the upper jaw, the lower jaw, and the temporomandibular joints in width, depth, and height.

As shown in FIG. 18, the imaging region rc for the third living organ is located between the respective imaging regions rr and rl for the first and second living organs and is continuous with the imaging region rr and the imaging region rl.

Since the three regions are continuous without any break, CT imaging data for the whole of the imaging target portions without any break can be obtained.

The imaging region rr, the imaging region rl, and the imaging region rc may be specified by the operator using the imaging region specifying part 83 as discussed earlier and may be positionally set in advance with respect to, for example, the position of the subject holding part with the dental arch of a standard skeleton obtained statistically as a reference.

(The Third Preferred Embodiment)

The medical X-ray CT imaging apparatus M or the X-ray image display device M2 of the third preferred embodiment displays CT images of the living organs symmetrically located with respect to a predetermined plane on one display screen of the display part 88 for comparison by using the cone beam B. Hereinafter, discussion will be made on display examples where the CT images of the living organs are displayed. Though discussion will be made mainly on the temporomandibular joints as the living organs in the third preferred embodiment, the present invention is not limited to this. Other portions may be adopted only if the portions are the living organs symmetrically located with respect to a predetermined plane.

Figure 20:
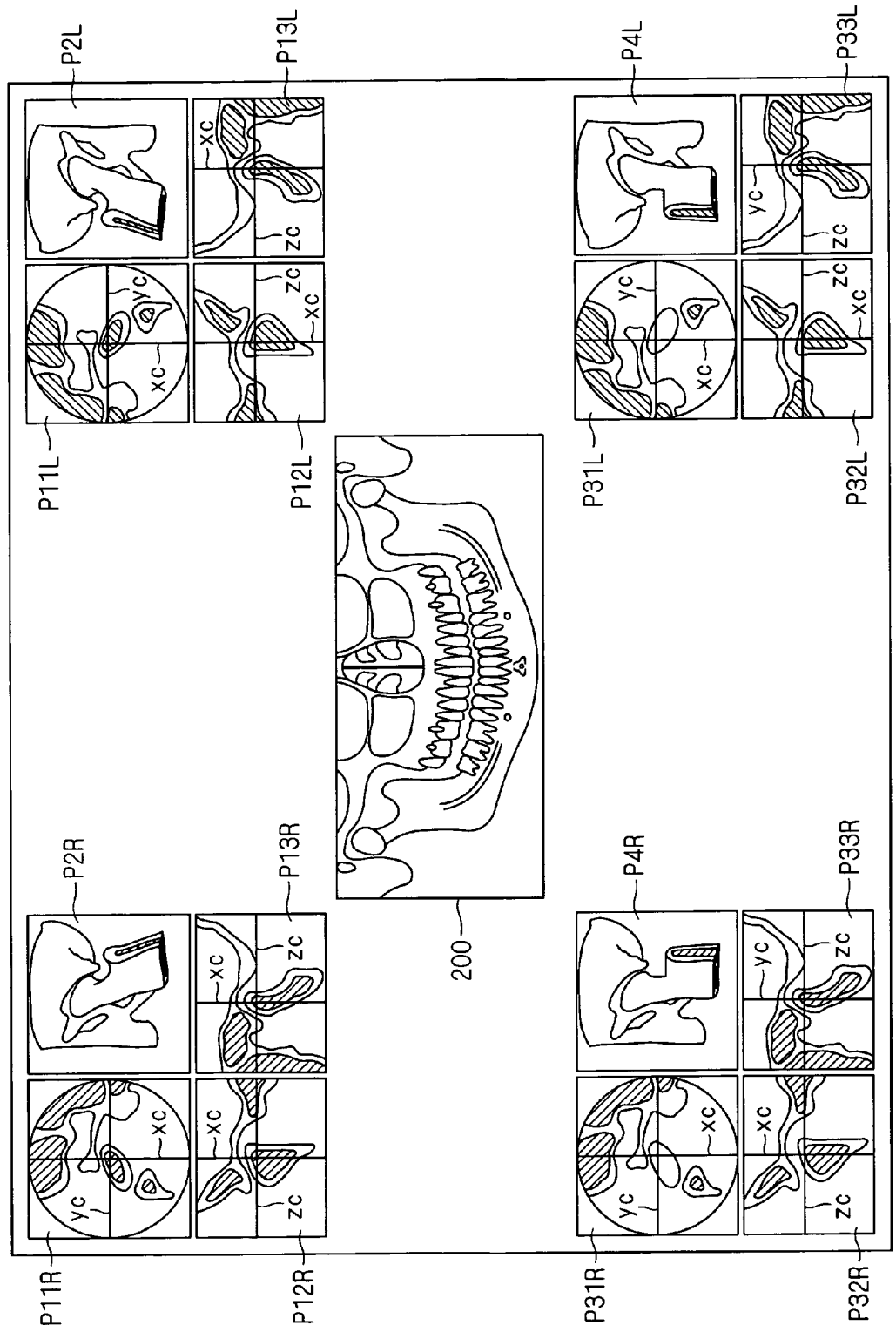
FIGS. 20 to 27 are views showing a display screen of the medical X-ray CT imaging apparatus M in accordance with a third preferred embodiment of the present invention.

In FIG. 20, first, shown is an exemplary case where the panoramic image 200 and the CT images of the temporomandibular joints in the closed and open states are displayed. In FIG. 20, the panoramic image 200 is displayed in the center and the CT images of the temporomandibular joints in the closed state are displayed on the upper stage and the CT images of the temporomandibular joints in the open state are displayed on the lower stage. Among the CT images on the upper stage of FIG. 20, the cross sectional CT images P11R to P13R of the right-side temporomandibular joint in the closed state and the volume rendering image P2R of the right-side temporomandibular joint are displayed on the left side of the screen, and the cross sectional CT images P11L to P13L of the left-side temporomandibular joint in the closed state and the volume rendering image P2L of the left-side temporomandibular joint are displayed on the right side of the screen. Among the CT images on the lower stage of FIG. 20, the cross sectional CT images P31R to P33R of the right-side temporomandibular joint in the open state and the volume rendering image P4R of the right-side temporomandibular joint are displayed on the left side of the screen, and the cross sectional CT images P31L to P33L of the left-side temporomandibular joint in the open state and the volume rendering image P4L of the left-side temporomandibular joint are displayed on the right side of the screen.

The panoramic image 200 may be an image reconstructed from the data obtained by CT imaging of the subject o or an image captured by panoramic radiography. Alternatively, an image captured in the past may be read out from the storage part 82 to be used.

Figure 21:
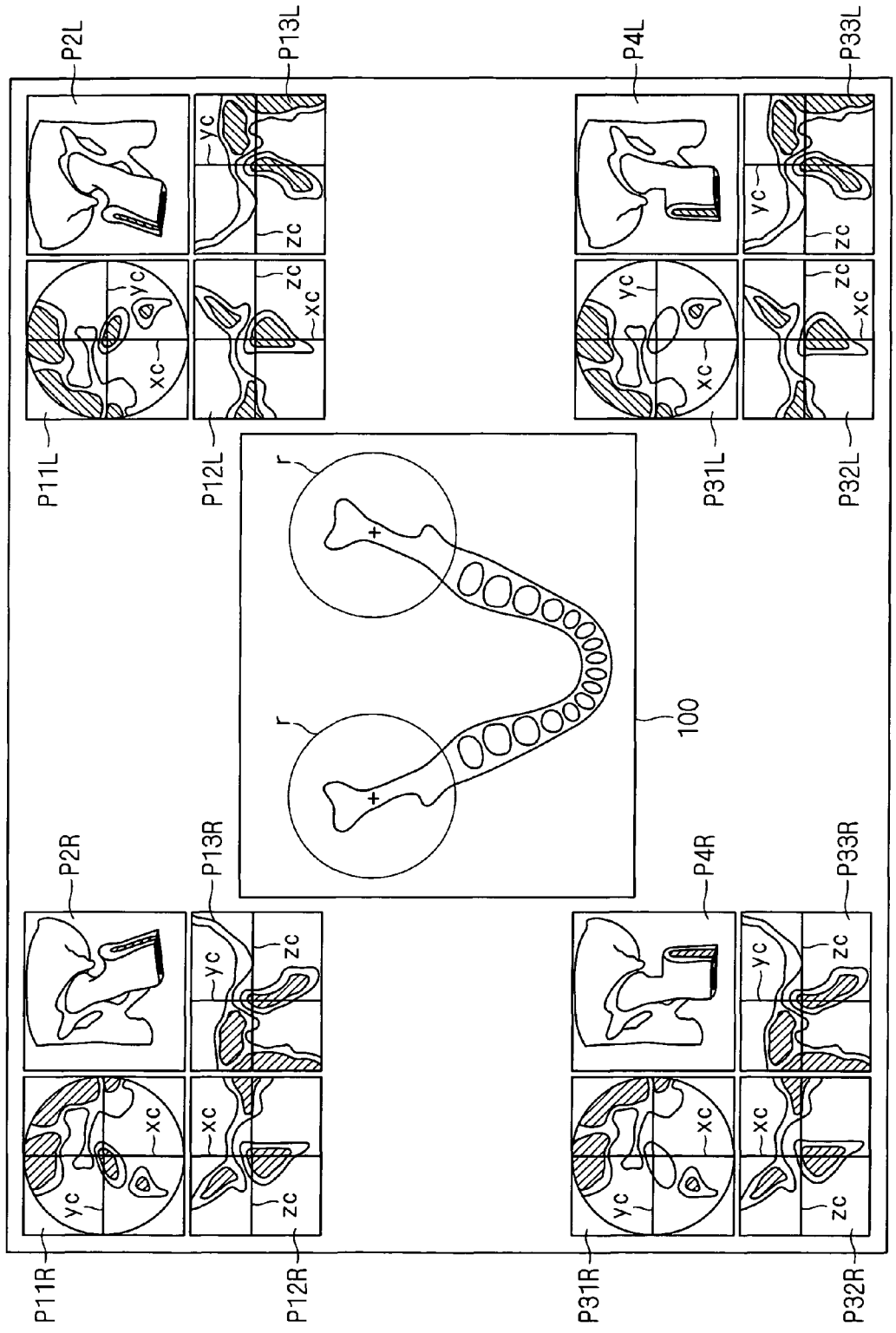

Thus, by displaying the panoramic image 200 and the CT images of the temporomandibular joints in the closed and open states for comparison, it is possible to examine the closed and open states of the temporomandibular joints while observing the entire dental arch including the temporomandibular joints in the panoramic image 200 and therefore possible to support efficient diagnoses and effective explanations for patients. Further, in FIG. 21, shown is an exemplary case where the illustration 100 of the dental arch including the temporomandibular joints and the CT images of the temporomandibular joints in the closed and open states are displayed. In FIG. 21, the illustration 100 is displayed in the center and the CT images of the temporomandibular joints in the closed state are displayed on the upper stage and the CT images of the temporomandibular joints in the open state are displayed on the lower stage. Among the CT images on the upper stage of FIG. 21, the cross sectional CT images P11R to P13R of the right-side temporomandibular joint in the closed state and the volume rendering image P2R of the right-side temporomandibular joint are displayed on the left side of the screen, and the cross sectional CT images P11L to P13L of the left-side temporomandibular joint in the closed state and the volume rendering image P2L of the left-side temporomandibular joint are displayed on the right side of the screen. Among the CT images on the lower stage of FIG. 21, the cross sectional CT images P31R to P33R of the right-side temporomandibular joint in the open state and the volume rendering image P4R of the right-side temporomandibular joint are displayed on the left side of the screen, and the cross sectional CT images P31L to P33L of the left-side temporomandibular joint in the open state and the volume rendering image P4L of the left-side temporomandibular joint are displayed on the right side of the screen.

Though the illustration 100 of the dental arch including the temporomandibular joints is used in FIG. 21, the present invention is not limited to such a case but CT images of the teeth and jaw region including both the temporomandibular joints may be reconstructed from the data obtained by CT imaging of the subject o, to be used. Further, as the image corresponding to the illustration 100, an image captured in the past may be read out from the storage part 82 to be used.

Thus, also by displaying the illustration 100 and the CT images of the temporomandibular joints in the closed and open states for comparison, it is possible to examine the closed and open states of the temporomandibular joints while recognizing the positions of the temporomandibular joints in the illustration 100 showing the entire dental arch and therefore possible to support efficient diagnoses and effective explanations for patients.

Figure 22:
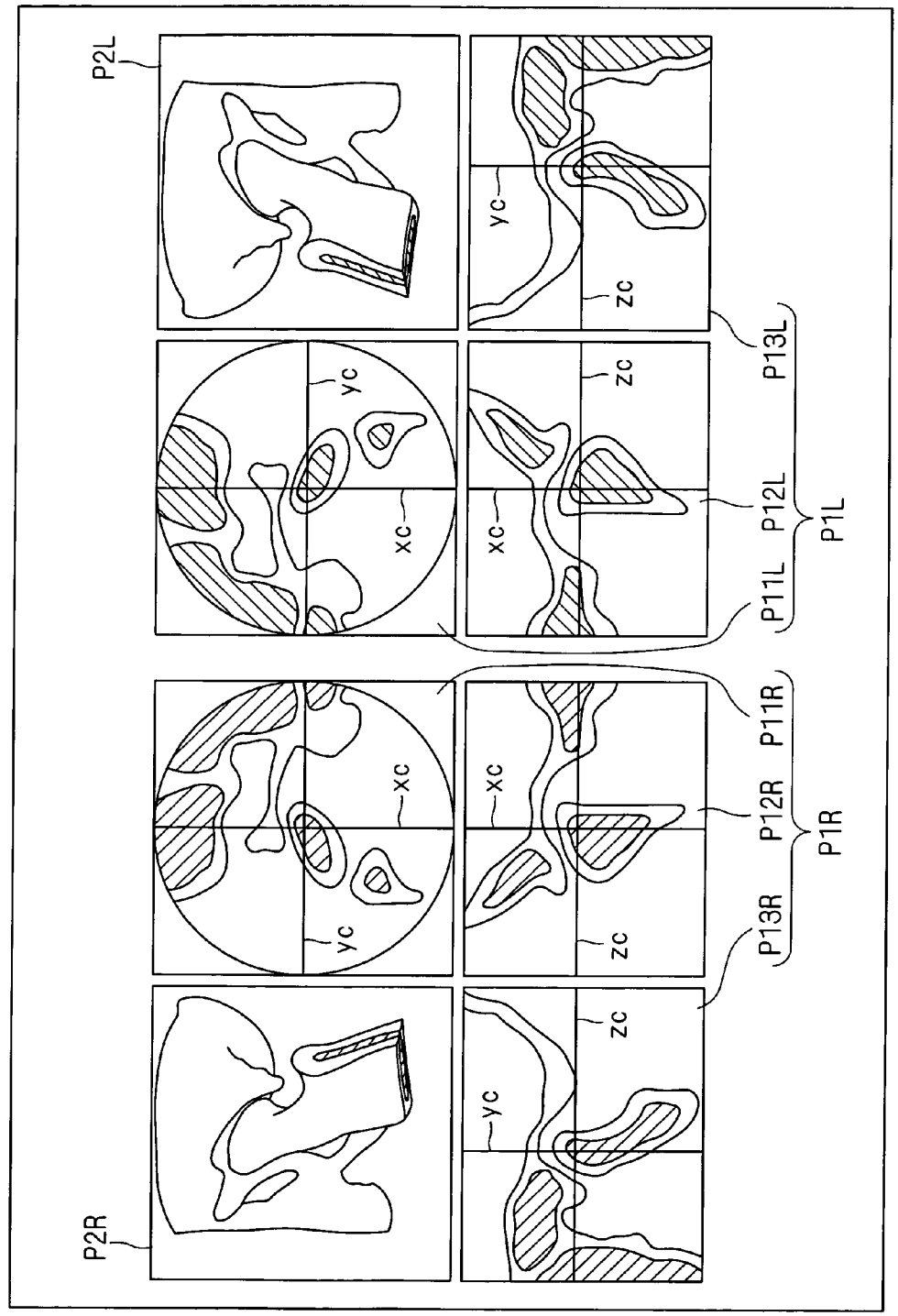

In FIG. 22, shown is an exemplary case where the CT images of the temporomandibular joints in the closed state are displayed in an arrangement different from that of FIG. 16. In FIG. 22, like in FIG. 16, the cross sectional CT image P1R of the right-side temporomandibular joint in the closed state and the volume rendering image P2R of the right-side temporomandibular joint are displayed on the left side of the screen, and the cross sectional CT image P1L of the left-side temporomandibular joint in the closed state and the volume rendering image P2L of the left-side temporomandibular joint are displayed on the right side of the screen. In FIG. 22, however, unlike in FIG. 16, the volume rendering image P2R of the right-side temporomandibular joint is displayed in the upper left, the cross sectional CT image P11R of the right-side temporomandibular joint sectioned by the xy plane is displayed in the upper right, the cross sectional CT image P12R of the right-side temporomandibular joint sectioned by the xz plane is displayed in the lower right, and the cross sectional CT image P13R of the right-side temporomandibular joint sectioned by the yz plane is displayed in the lower left. The arrangement of the cross sectional CT image P1L of the left-side temporomandibular joint in the closed state and the volume rendering image P2L of the left-side temporomandibular joint is the same as that of FIG. 16.

By displaying the CT images of the right-side temporomandibular joint and the cross sectional CT images of the left-side temporomandibular joint in mirror symmetry, the images can be displayed in a form close to the actual arrangement of the temporomandibular joints, and it is therefore possible to support efficient diagnoses and effective explanations for patients.

Figure 23:
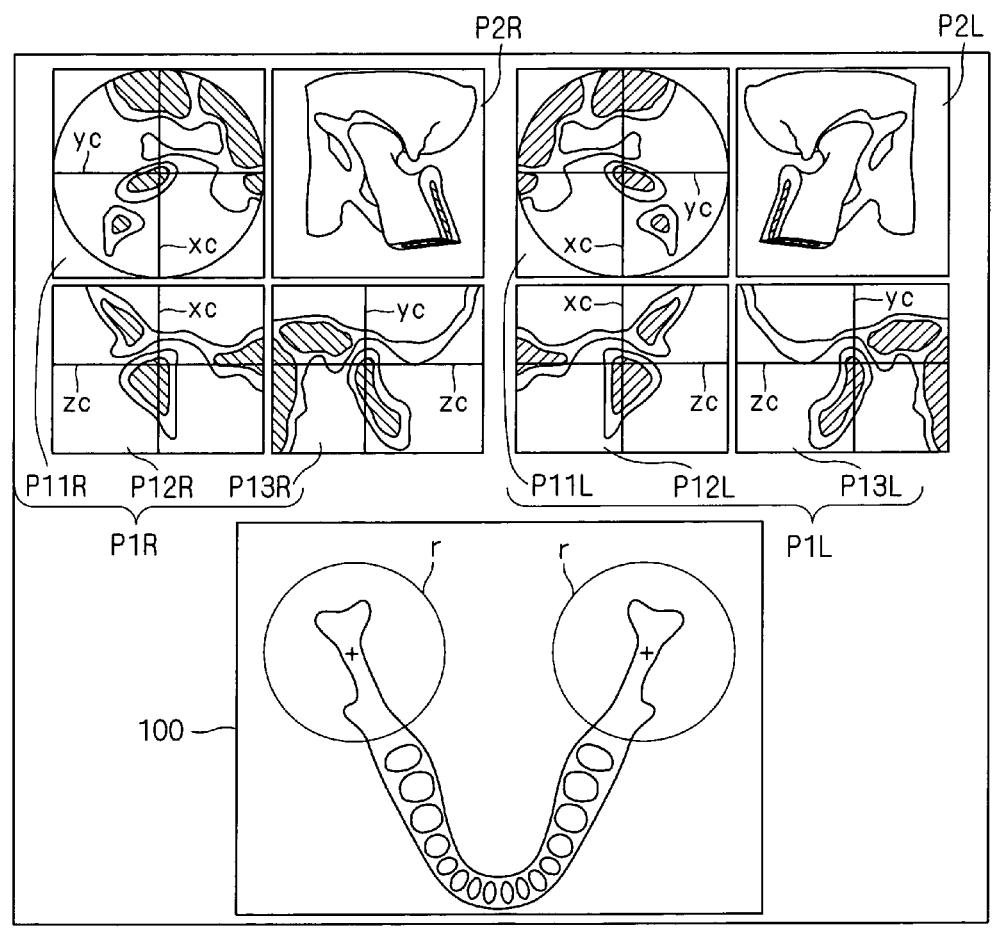
Figure 24:
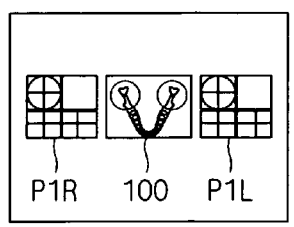

In FIG. 23, unlike in FIG. 21, displayed are the illustration 100 of the dental arch including the temporomandibular joints and the CT images of the temporomandibular joints in the closed state. In FIG. 23, the cross sectional CT images P11R to P13R of the right-side temporomandibular joint in the closed state and the volume rendering image P2R of the right-side temporomandibular joint are displayed on the left side of the upper stage of the screen, and the cross sectional CT images P11L to P13L of the left-side temporomandibular joint in the closed state and the volume rendering image P2L of the left-side temporomandibular joint are displayed on the right side of the upper stage of the screen. Further, in FIG. 23, the illustration 100 of the dental arch including the temporomandibular joints is displayed on the lower stage of the screen. The CT images of the temporomandibular joints in the closed state may be displayed in the same layout, instead of the CT images of the temporomandibular joints in the open state. The display manner of the illustration 100 of the dental arch including the temporomandibular joints and the CT images of the temporomandibular joints in the closed state is not limited to that of FIG. 23 but the illustration 100 and the CT images of the temporomandibular joints in the closed state may be displayed in a row as shown in FIG. 24.

Thus, by displaying the illustration 100 of the dental arch including the temporomandibular joints and the CT images of the temporomandibular joints in the closed state, it is possible to take a view of the whole and therefore possible to support efficient diagnoses and effective explanations for patients.

Figure 25:
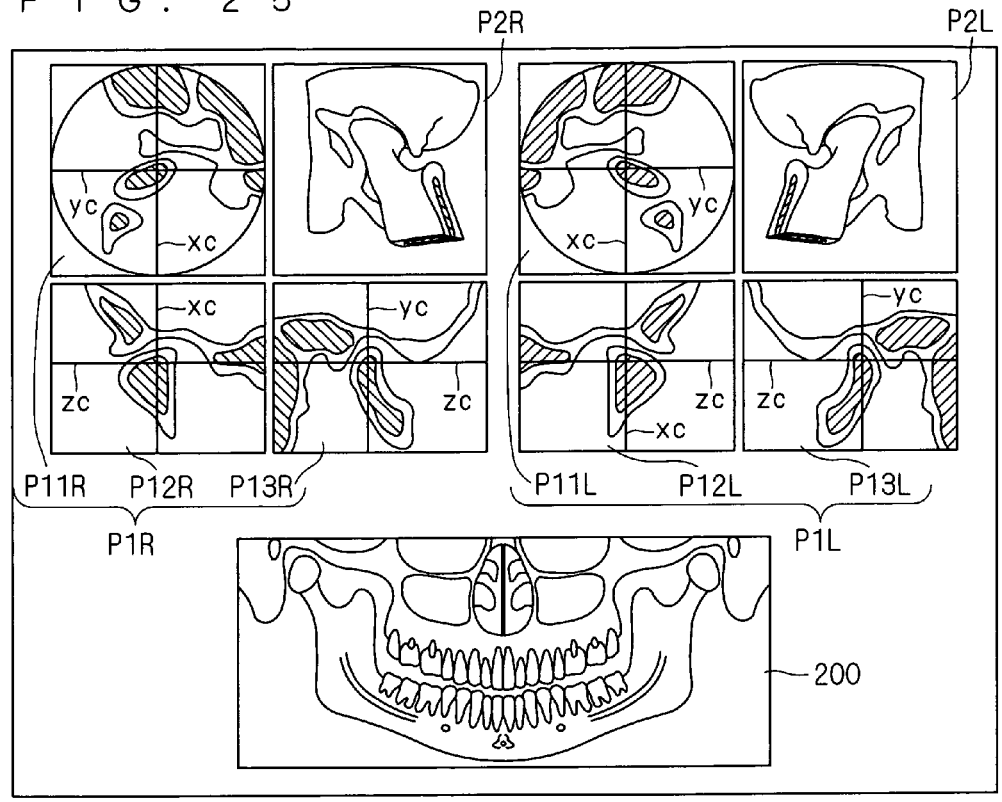
Figure 26:
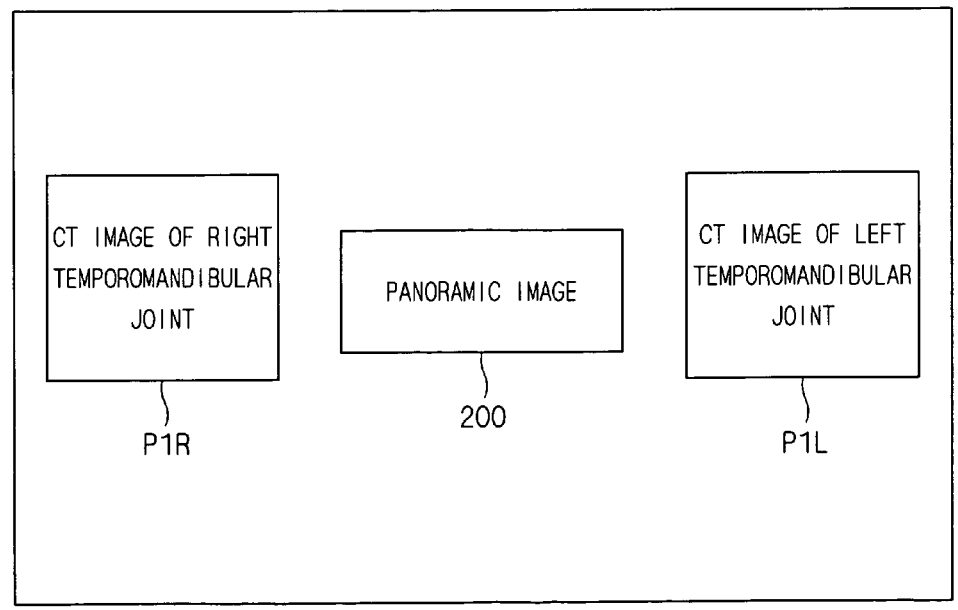

In FIG. 25, unlike in FIG. 20, displayed are the panoramic image 200 and the CT images of the temporomandibular joints in the closed state. In FIG. 25, the cross sectional CT images P11R to P13R of the right-side temporomandibular joint in the closed state and the volume rendering image P2R of the right-side temporomandibular joint are displayed on the left side of the upper stage of the screen, and the cross sectional CT images P11L to P13L of the left-side temporomandibular joint in the closed state and the volume rendering image P2L of the left-side temporomandibular joint are displayed on the right side of the upper stage of the screen. Further, in FIG. 25, the panoramic image 200 is displayed on the lower stage of the screen. The CT images of the temporomandibular joints in the closed state may be displayed in the same layout, instead of the CT images of the temporomandibular joints in the open state. The display manner of the panoramic image 200 and the CT images of the temporomandibular joints in the closed state is not limited to that of FIG. 25 but the panoramic image 200 and the CT images of the temporomandibular joints in the closed state may be displayed in a row as shown in FIG. 26.

Thus, by displaying the panoramic image 200 and the CT images of the temporomandibular joints in the closed state, it is possible to take a view of the whole and therefore possible to support efficient diagnoses and effective explanations for patients.

Figure 27:
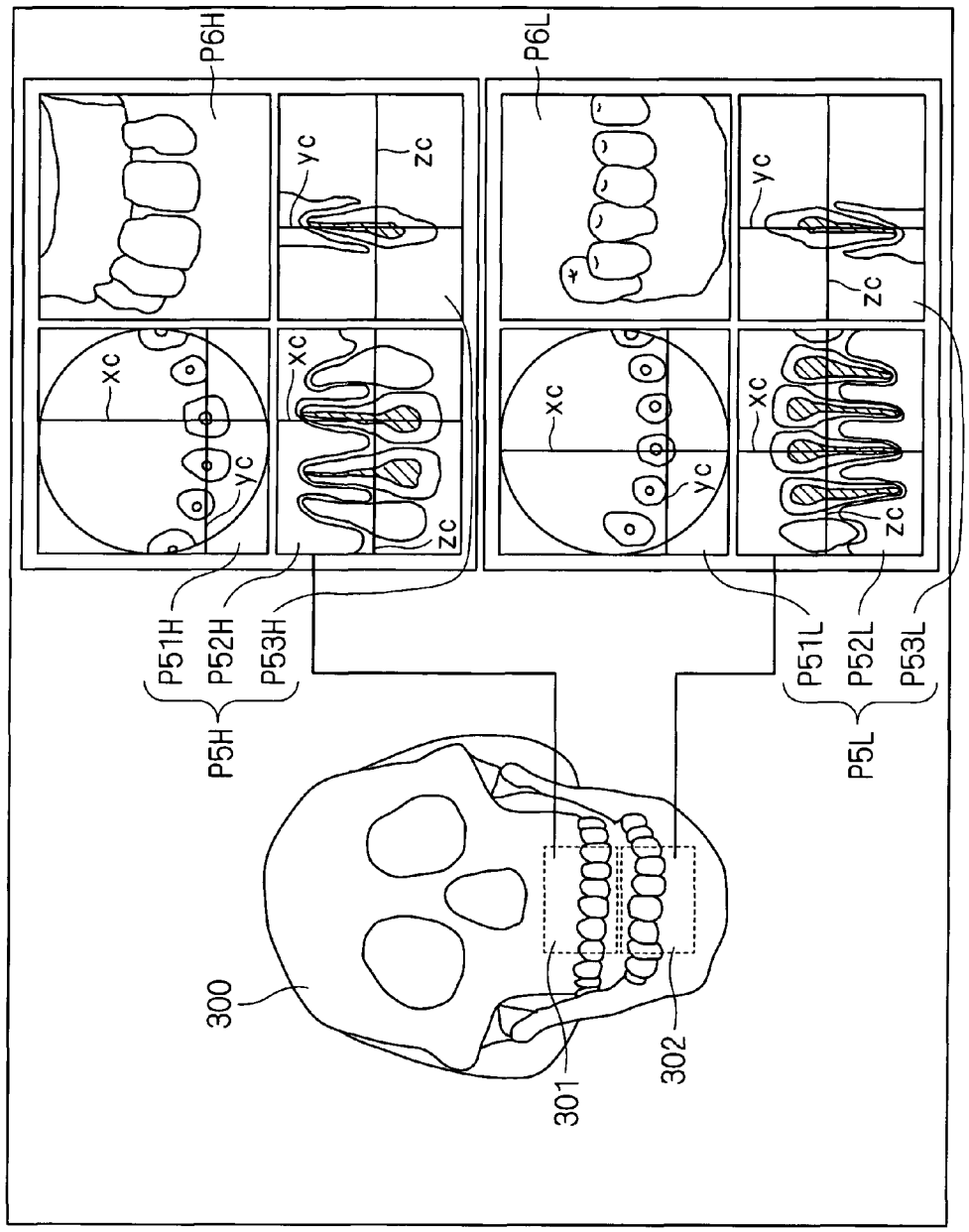

The above examples relate to the temporomandibular joints and discussion has been made on the CT images of the living organs symmetrically located with respect to a plane including the median line. The present invention, however, is not limited to the above case but CT images of the living organs which are vertically symmetrical with respect to a predetermined plane, such as an upper tooth row and a lower tooth row which are vertically symmetrical with respect to an occlusal surface, may be displayed. Now, discussion will be made on the medical X-ray CT imaging apparatus M which performs CT imaging on an upper tooth row and a lower tooth row. The medical X-ray CT imaging apparatus M uses an illustration 300 of a skull shown on the left side of FIG. 27 to specify an upper tooth row 301 and a lower tooth row 302 which are imaging regions r and moves the X-ray generation part 10 and the X-ray detection part 20 on the basis of the specified positions to perform CT imaging. The apparatus M reconstructs CT images on the basis of the data captured by the CT imaging and displays the CT images shown on the left side of FIG. 27 on the display part 88. In FIG. 27, the illustration 300 is displayed on the right side of the screen, and a CT image P5H of the upper tooth row 301 and a volume rendering image P6H of the upper tooth row 301 are displayed on the upper left of the screen, and a CT image P5L of the lower tooth row 302 and a volume rendering image P6L of the lower tooth row 302 are displayed on the lower left of the screen.

The CT image P5H includes a cross sectional CT image P51H of the upper tooth row 301 sectioned by the xy plane which is shown in the upper left, a cross sectional CT image P52H of the upper tooth row 301 sectioned by the xz plane which is shown in the lower left, and a cross sectional CT image P53H of the upper tooth row 301 sectioned by the yz plane which is shown in the lower right. The CT image P5L includes a cross sectional CT image P51L of the lower tooth row 302 sectioned by the xy plane which is shown in the upper left, a cross sectional CT image P52L of the lower tooth row 302 sectioned by the xz plane which is shown in the lower left, and a cross sectional CT image P53L of the lower tooth row 302 sectioned by the yz plane which is shown in the lower right. Though an actual occlusion has a deviation between the upper tooth row and the lower tooth row, the positions of the displayed cross sectional CT images P53H and P53L are adjusted so that these cross sectional CT images may be on the same y axis. Though the illustration 300 and the CT images of the upper tooth row and the lower tooth row are displayed in FIG. 27, the present invention is not limited to this but there may be a case where only the CT images of the upper tooth row and the lower tooth row are displayed.

It is desired to control the cone beam for the CT imaging to be emitted to only the imaging target portion, and for example, there is a possible configuration to control the vertical length of the cone beam to cover only one of the teeth of the upper jaw and those of the lower jaw. In this case, if the imaging target portion changes vertically, it is necessary to somehow adjust the position of the radiation field of the cone beam to the position of the imaging target portion.

In the exemplary configurations of FIGS. 5 and 6, specifically, the supporting part 30 may be moved up and down relative to the subject holding part 40, the subject holding part 40 may be moved up and down relative to the supporting part 30, or both the parts may be moved up and down mutually.

Figure 28:
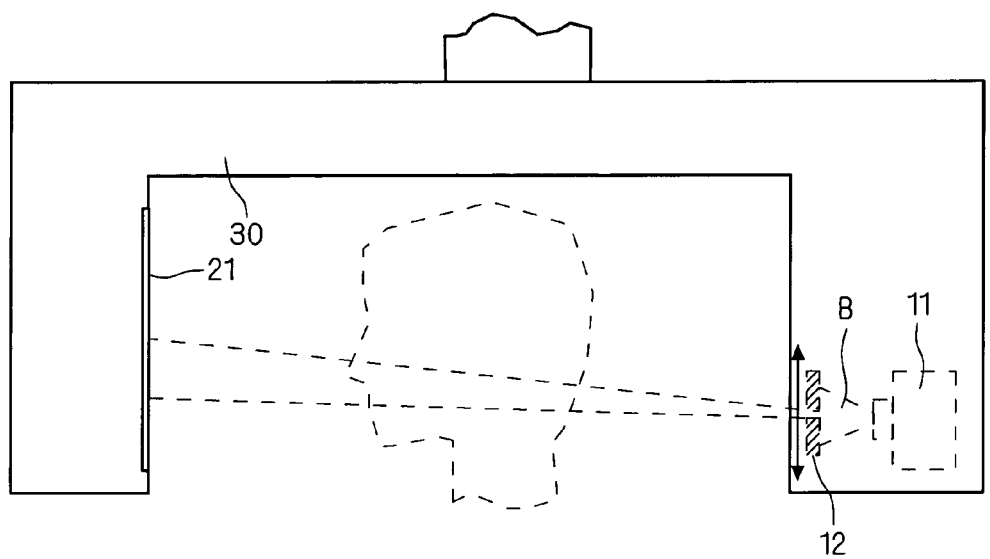
FIGS. 28 to 32 are views showing a state of emission of cone beams.
Figure 29:
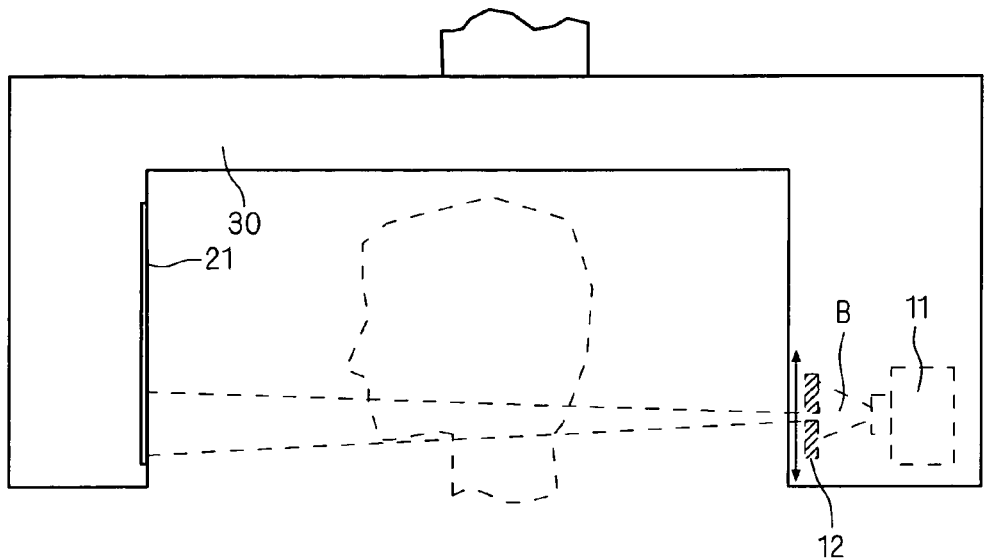

The Z-axis motor 60*z* for moving the supporting part 30 of FIGS. 7 and 9 may be driven to move the supporting part 30 up and down relative to the subject holding part 40, and the Z-axis motor 60*z* for moving the supporting part 30 of FIGS. 8 and 9 may be driven to move the subject holding part 40 up and down relative to the supporting part 30. As shown in the exemplary configurations of FIGS. 28 and 29, the radiation field control part 12 placed in front of the X-ray generator 11 may be moved up and down by a well-known and not-shown actuator using a motor or the like in a direction indicated by the arrow of the figures, to thereby control the cone beam to be projected upward or downward. FIG. 28 shows a case of irradiating the teeth of the upper jaw and FIG. 29 shows a case of irradiating the teeth of the lower jaw.

Figure 30:
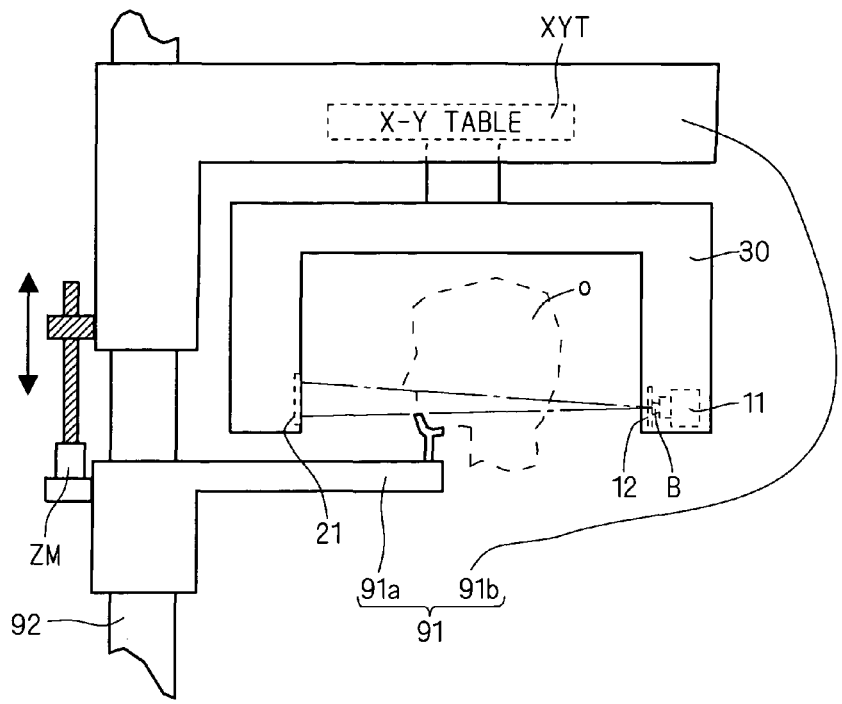
Figure 31:
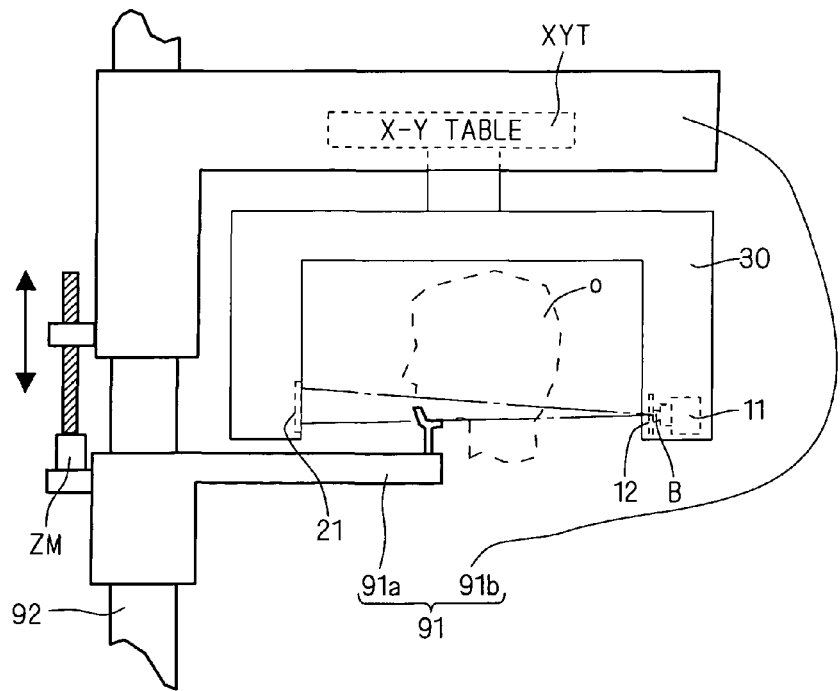

Further, as shown in FIGS. 30 and 31, there may be a configuration wherein the up-and-down moving frame 91 is constituted of an up-and-down moving frame lower part 91*a* provided with a chin rest on which the chin of a patient o as the subject is placed in order for the head to be held and an up-and-down moving frame upper part 91*b* which moves up and down relative to the up-and-down moving frame lower part 91*a* and the whole of the up-and-down moving frame lower part 91*a* and the up-and-down moving frame upper part 91*b* is moved relative to the column 92 by a not-shown moving mechanism, to be thereby vertically positioned, and then the up-and-down moving frame upper part 91*b* can move up and down relative to the up-and-down moving frame lower part 91*b*, to be adjusted to the target portion of the CT imaging.

In the exemplary configuration of FIGS. 30 and 31, the up-and-down moving frame lower part 91*a* is provided with an up-and-down movement driving motor ZM including a thread axis having a longitudinal axis in the direction of vertical movement of the up-and-down moving frame upper part 91*b*, part of the up-and-down moving frame upper part 91*b* serves as an internal thread to be in threaded engagement with the thread axis, and the up-and-down moving frame upper part 91*b* can be moved up and down relative to the up-and-down moving frame lower part 91*b* by the drive of the up-and-down movement driving motor ZM. FIG. 30 shows a case of irradiating the teeth of the upper jaw, and FIG. 31 shows a case of irradiating the teeth of the lower jaw.

Figure 32:
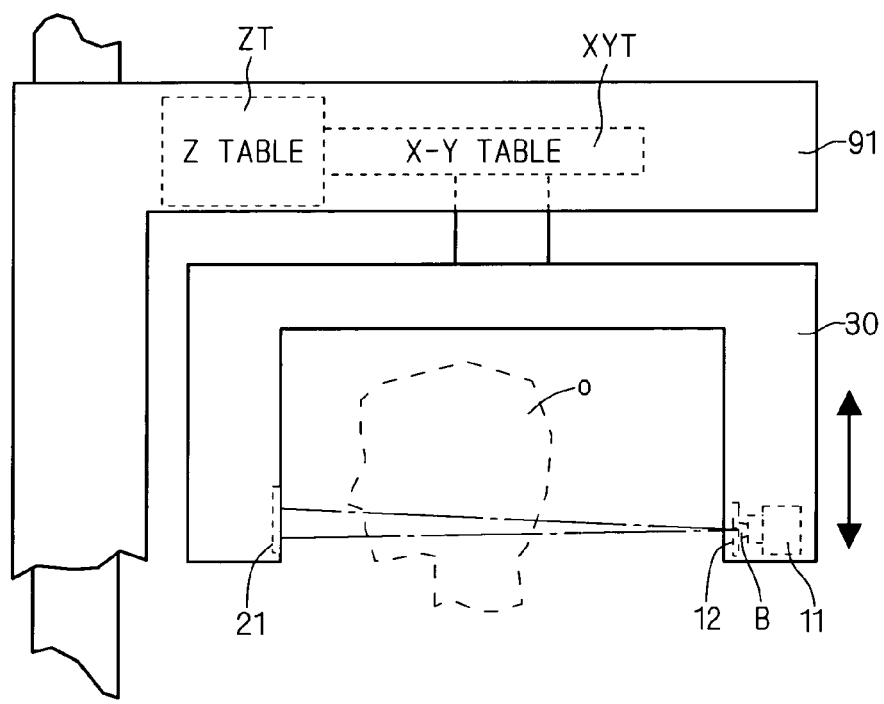

Further, as shown in FIG. 32, there may be a case where an XY table XYT having the same tables as the X table 35X and the Y table 35Y shown in FIG. 2, which axially supports the supporting part 30, and a Z table ZT for moving the XY table XYT up and down are provided inside the up-and-down moving frame 91 and the supporting part 30 is moved up and down relative to the subject o or the subject holding part 40, whereby the radiation field of the cone beam is controlled to be directed upward or downward. FIG. 32 shows a case of irradiating the teeth of the upper jaw. The case of irradiating the teeth of the lower jaw is almost the same as the cases shown in FIGS. 29 and 31 and will not therefore be shown. In FIGS. 28 to 32, the constituent elements common to those of FIGS. 1 to 9 are represented by the same reference signs and detailed description thereof will be omitted.

FIG. 33 shows an example of image display in a case where serial CT imaging is performed on the first living organ, the second living organ, and the third living organ such as the right living organ, the left living organ ol, and the central living organ oc discussed earlier with reference to FIG. 18.

The CT imaging data obtained by the CT imaging of the first living organ is defined as first living organ CT imaging data io1, the CT imaging data obtained by the CT imaging of the second living organ is defined as second living organ CT imaging data io2, and the CT imaging data obtained by the CT imaging on the third living organ is defined as third living organ CT imaging data io3.

The image operation part 84 performs position calculation on the first living organ CT imaging data io1, the second living organ CT imaging data io2, and the third living organ CT imaging data io3 so that actual positions of the first living organ, the second living organ, and the third living organ in the living body can be reflected with fidelity, to thereby synthesize one CT imaging data ios.

The position calculation for synthesis may be performed, for example, by measuring the positions of the imaging region rr, the imaging region rl, and the imaging region rc from the amount of movement of the rotation arm during the serial CT imaging of the first living organ, the second living organ, and the third living organ and reflecting the respective positions of the imaging region rr, the imaging region rl, and the imaging region rc on the arrangement of the first living organ CT imaging data io1, the second living organ CT imaging data io2, and the third living organ CT imaging data io3 with fidelity in the synthesizing operation.

Though the actual CT imaging data is not visible data until being reconstructed and displayed, the synthesized CT imaging data ios is schematically shown in FIG. 34.

P71, P72, P73, and Pv1 in FIG. 33 show CT images obtained by reconstructing the synthesized CT imaging data ios.

The cross sectional CT image P7 includes the cross sectional CT image P71 of the left and right temporomandibular joints sectioned by the xy plane which is shown in the upper right, the cross sectional CT image P72 of the left and right temporomandibular joints sectioned by the xz plane which is shown in the lower right, and the cross sectional CT image P73 of the left-side temporomandibular joint sectioned by the yz plane which is shown in the lower left, and these cross sectional CT images are displayed. Like in FIG. 13 and the like, the x cursor xc, the y cursor yc, and the z cursor zc are also displayed. In the upper left, a volume rendering image Pv1 showing only the left-side temporomandibular joint is also displayed.

Since the volume rendering image Pv is shown in FIG. 16 and other figures, the image is represented by a simplified shape in FIG. 25.

Figure 35:
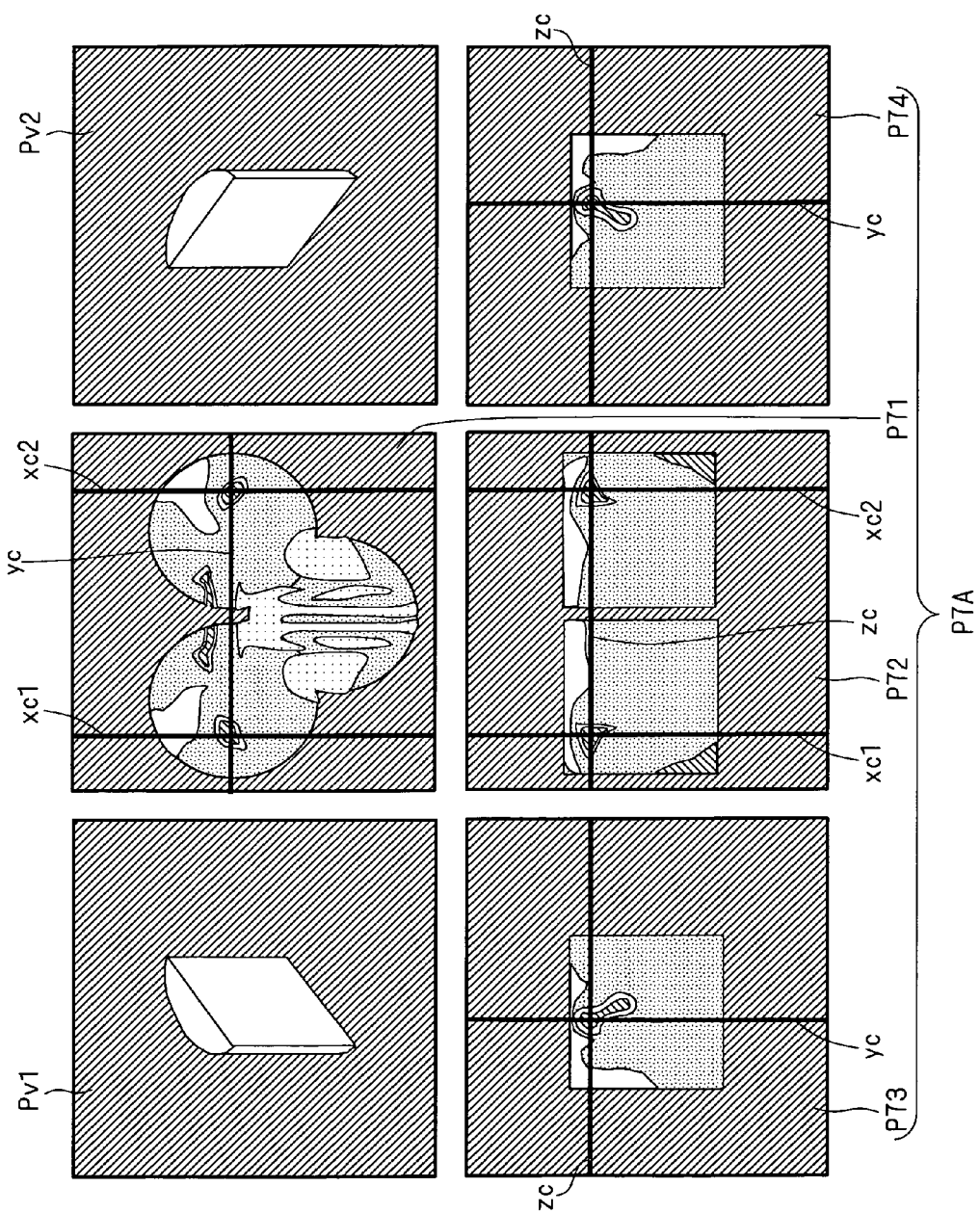
FIGS. 35 and 36 are views showing another example of image display in the case where the serial CT imaging is performed on the first living organ, the second living organ, and the third living organ.

FIG. 35 shows an exemplary display where the CT image of FIG. 33 is further developed.

The display of FIG. 35 is basically the same as that of FIG. 25 but different therefrom in that two x cursors xc1 and xc2 indicating the positions of two yz planes of which the positions are different, a cross sectional CT image P74 showing a section cut by another yz plane and a volume rendering image Pv2 showing only the right-side temporomandibular joint are also displayed.

A cross sectional CT image P7A includes the cross sectional CT image P71, the cross sectional CT image P72, the cross sectional CT image P73, and the cross sectional CT image P74.

As a matter of course, both the x cursors xc1 and xc2 can be moved and both the yz plane shown in P73 and the yz plane shown in P74 can be changed.

Such a display allows the first living organ and the second living organ to be displayed for comparison, and it is therefore possible to perform more effective diagnoses.

Though FIG. 33 shows the exemplary image display of the synthesized image obtained by combining the CT imaging data of the third living organ with the CT imaging data of the first living organ and the second living organ when the serial CT imaging is performed on the first living organ, the second living organ, and the third living organ, the generation of the CT imaging data by performing position calculation so that actual positions of the organs in the living body can be reflected with fidelity may be performed only on the first living organ and the second living organ.

Figure 19:
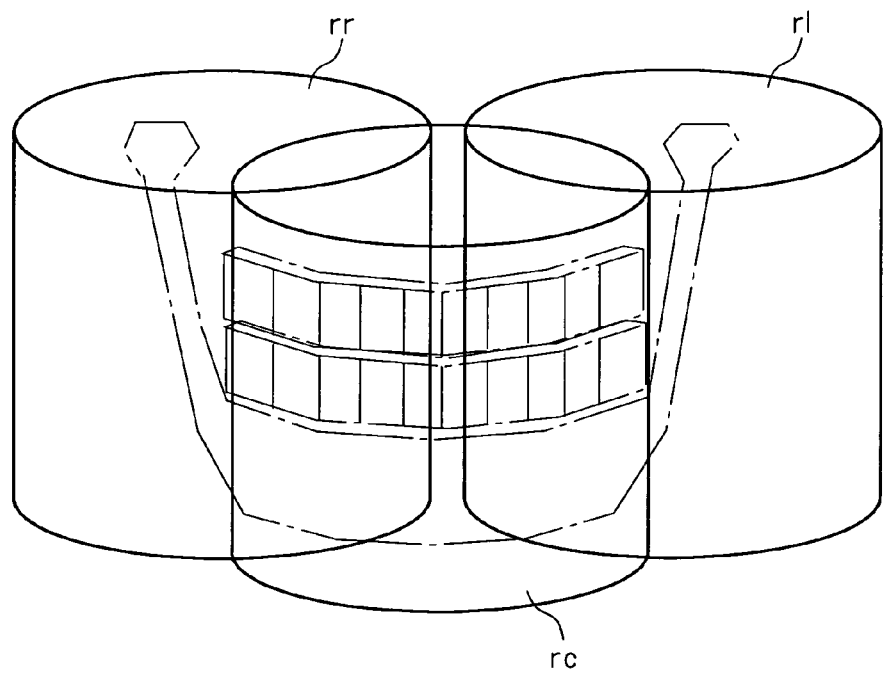
Figure 36:
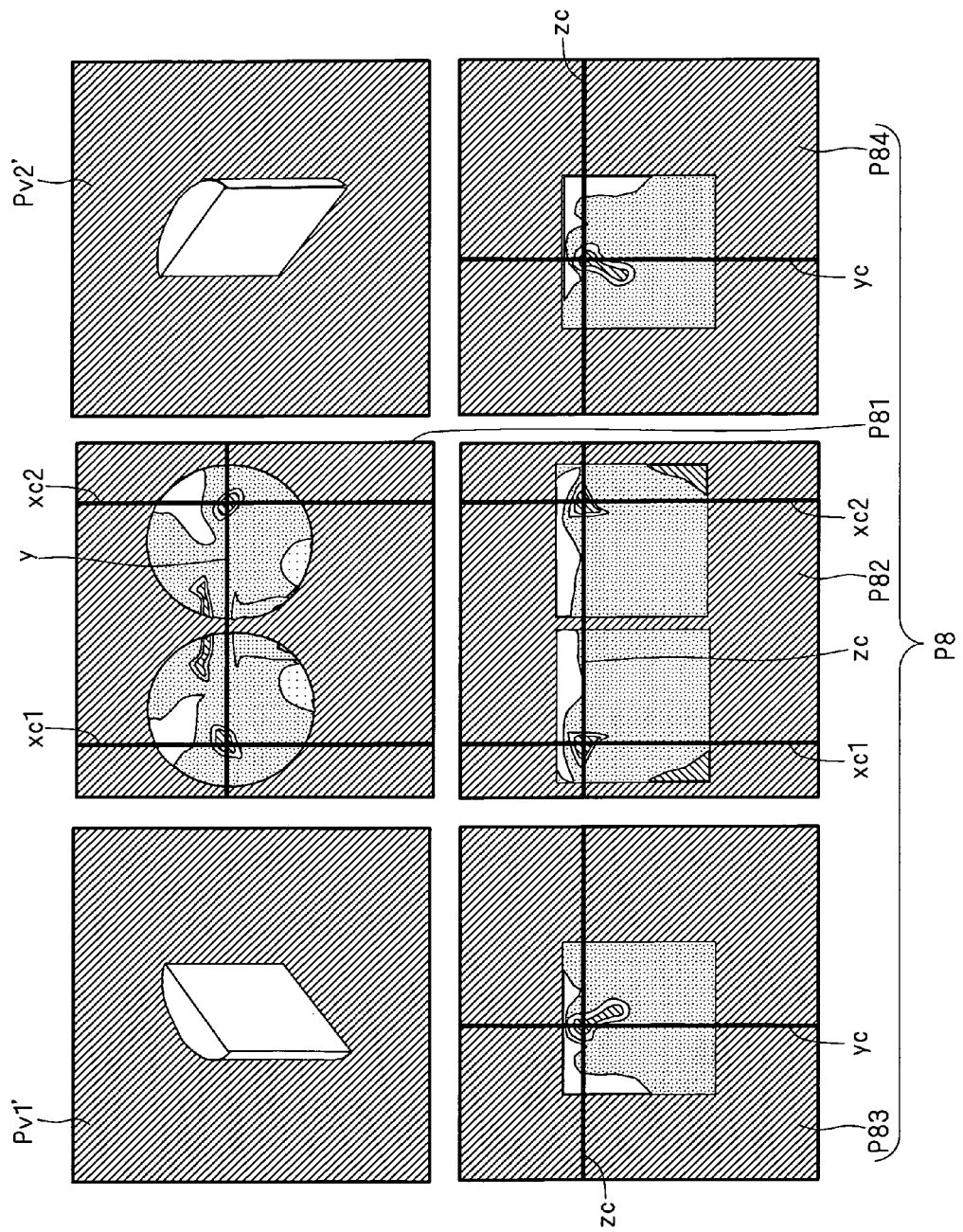

FIG. 36 shows an exemplary display of the reconstructed CT imaging data, where the image operation part 84 performs position calculation on the first living organ CT imaging data io1 and the second living organ CT imaging data io2 described with reference to FIG. 19 so that actual positions of the first living organ and the second living organ in the living body can be reflected with fidelity, to thereby synthesize one CT imaging data ios' which is not shown, and the CT imaging data is reconstructed.

There may be a case where the serial CT imaging is performed, as discussed with reference to FIG. 18, on the first living organ, the second living organ, and the third living organ such as the right living organ, the left living organ ol, and the central living organ oc discussed earlier and only the CT imaging data of the first living organ and the second living organ are combined to be displayed, with the CT imaging data of the third living organ excluded from the data to be combined, or there may be another case where the imaging is performed only on the first living organ and the second living organ and then the CT imaging data of the first living organ and the second living organ are combined to be displayed.

In the case where the imaging is performed only on the first living organ and the second living organ and then the CT imaging data of the first living organ and the second living organ are combined, the operation therefor is as follows.

Assuming that the right-side temporomandibular joint and the portions in the vicinity thereof are defined as the right-side living organ or and the left-side temporomandibular joint and the portions in the vicinity thereof are defined as the left-side living organ ol, the right-side imaging region rr for the CT imaging of the right-side living organ or and the left-side imaging region rl for the CT imaging of the left-side living organ ol are set.

The CT imaging is performed consecutively on the imaging region rr and the imaging region rl, but as to the sequence of imaging, any one of these may be first.

Herein, it is assumed that one of the right-side living organ or and the left-side living organ of is defined as the first living organ.

The imaging region rr and the imaging region rl may be specified by the operator using the imaging region specifying part 83 as discussed earlier or may be positionally set in advance with respect to the position of the subject holding part with the dental arch of a standard skeleton obtained statistically as a reference.

Hereinafter, the synthesis and display of the CT imaging data are common to the case where the serial CT imaging is performed on the first living organ, the second living organ, and the third living organ and only the CT imaging data of the first living organ and the second living organ are combined to be displayed, with the CT imaging data of the third living organ excluded from the data to be combined, and the case where the imaging is performed only on the first living organ and the second living organ and then the CT imaging data of the first living organ and the second living organ are combined to be displayed.

The CT imaging data obtained by the CT imaging of the first living organ is defined as first living organ CT imaging data io1, and the CT imaging data obtained by the CT imaging of the second living organ is defined as second living organ CT imaging data io2.

The image operation part 84 performs position calculation on the first living organ CT imaging data io1 and the second living organ CT imaging data io2 so that actual positions of the first living organ and the second living organ in the living body can be reflected with fidelity, to thereby synthesize one CT imaging data ios'.

The position calculation for synthesis may be performed, for example, by measuring the positions of the imaging region rr and the imaging region rl from the amount of movement of the rotation arm during the serial CT imaging of the first living organ and the second living organ and reflecting the respective positions of the imaging region rr and the imaging region rl on the arrangement of the first living organ CT imaging data io1 and the second living organ CT imaging data io2 with fidelity in the synthesizing operation.

P81, P82, P83, P84 and Pv in FIG. 36 show CT images obtained by reconstructing the synthesized CT imaging data ios.

The cross sectional CT image P8 includes the cross sectional CT image P81 of the left and right temporomandibular joints sectioned by the xy plane which is shown in the upper right, the cross sectional CT image P82 of the left and right temporomandibular joints sectioned by the xz plane which is shown in the lower right, the cross sectional CT image P83 of the left-side temporomandibular joint sectioned by the yz plane which is shown in the lower left, and the cross sectional CT image P84 of the right-side temporomandibular joint sectioned by the yz plane which is shown in the lower right, and these cross sectional CT images are displayed.

A volume rendering image Pv1' showing only the left-side temporomandibular joint is displayed in the upper left, and a volume rendering image Pv2' showing only the right-side temporomandibular joint is displayed in the upper right.

The x cursor xc, the y cursor yc, and the z cursor zc are also displayed like in FIG. 16 and other figures, but the two x cursors xc1 and xc2 indicating the positions of the two yz planes of which the positions are different are displayed unlike FIG. 16 and other figures.

As a matter of course, both the x cursors xc1 and xc2 can be moved and both the yz plane shown in P83 and the yz plane shown in P84 can be changed.

Since the volume rendering images Pv1' and Pv2' are shown in FIG. 16 and other figures, the images are represented by simplified shapes in FIG. 36.

Such a display allows the first living organ and the second living organ to be displayed for comparison, and it is therefore possible to perform more effective diagnoses.

Further, the configuration of the present invention can be applied not only to the case where the local CT imaging is performed on only the first living organ and the second living organ or the like but also to a case where with respect to the CT imaging data obtained by CT imaging of a wide region, e.g., an entire head, including the first living organ and the second living organ or the like, the first living organ and the second living organ are specified and images of only the specified region are reconstructed.

For example, if the detection surface of the X-ray detector 21 has an area which is wide enough to perform radiography of the entire head and the collimator of the radiation field control part 12 has an area which corresponds to the area of the detection surface, it is possible to perform CT imaging of the entire head.

In the medical X-ray CT imaging apparatus M which performs the CT imaging of the entire head and acquires X-ray imaging data, the above-discussed specification of the first living organ and the second living organ may be performed. In this case, performed is specification of the region to be displayed out of the X-ray imaging data.

For position specification, the above-discussed illustration may be displayed or any operation means such as buttons may be used. X-ray images which are actually captured may be displayed and used for position specification. When the CT imaging of the entire head is performed, a volume rendering image of the entire head may be displayed for position specification.

There may be a case where assuming general physique and skeleton, the positions for the first living organ and the second living organ are set as targets and by selecting a mode of displaying the first living organ and the second living organ, the first living organ and the second living organ are automatically displayed.

The first living organ and the second living organ may be automatically displayed by selecting the size group of the subject, for example, whether adult or child or sex. In this case, there may be a configuration wherein after specification of the first living organ and the second living organ, a target range is cut out of the reconstructed data and displayed, and there may be another configuration wherein after specification of the first living organ and the second living organ, the image processing of X-ray imaging data of the target range is performed.

Further, a third living organ may also be displayed.

As a matter of course, in the case where the CT imaging of the entire head is performed to acquire the X-ray imaging data and then the specification of the first living organ and the second living organ is performed, if the specified positions of the first living organ and the second living organ are not desired one, the positions to be set may be changed.

There may be a case where the specification of the first living organ and the second living organ or the specification of the first living organ, the second living organ, and the third living organ is performed first and then the CT imaging of the entire head is performed.

In any case, recognition and calculation on the three-dimensional space are the same as those in the earlier-discussed cases.

The configuration wherein the specification of the first living organ and the second living organ is performed and then the CT imaging of only the first living organ and the second living organ is performed has the advantage that the X-ray radiation exposure dose for the subject can be reduced. The configuration wherein the CT imaging of the entire head is performed to acquire the X-ray imaging data and then the specification of the first living organ and the second living organ is performed has the advantage in the degree of freedom where the target positions to be set as to the first living organ and the second living organ can be changed for the CT imaging data obtained by one CT imaging.

The invention claimed is:

1. A medical X-ray CT image display method which is a method of displaying medical X-ray CT images which are CT images obtained by X-ray CT imaging, using a cone beam, of a first living organ and a second living organ which are symmetrically located with respect to a predetermined plane, wherein
said CT image of said first living organ and said CT image of said second living organ are arranged on one display screen for comparison,
said CT image of said first living organ and said CT image of said second living organ are displayed with three cross-sectional planes which are orthogonal to one another, and
when an imaging region of one of said first living organ and said second living organ is specified and an arbitrary cross sectional CT image thereof is displayed, a corresponding cross sectional CT image of the imaging region of the other living organ, which is located symmetrically to the specified imaging region with respect to said predetermined plane, is automatically displayed on the same display screen for comparison.

2. The medical X-ray CT image display method according to claim 1, wherein
arbitrary said three cross-sectional planes are set with respect to each of said CT images of said first living organ and said second living organ,
said three cross-sectional planes and cursors associated with said three cross-sectional planes are displayed for each of said first and second living organs, and
by moving one of said cursors in any one of said three cross-sectional planes of one of said first and second living organs, said cursors in said three cross-sectional planes of the other living organ are also moved symmetrically with respect to said predetermined plane and a cross sectional CT image obtained at the position of said cursor with respect to each of said first living organ and said second living organ is displayed.

3. The medical X-ray CT image display method according to claim 1, further comprising the step of:
combining respective CT imaging data of said first living organ and said second living organ and CT imaging data of a third living organ located between said first living organ and said second living organ to synthesize a CT image and displaying said CT image.

4. A medical X-ray CT image display device, comprising:
a CT image acquisition part for acquiring CT images obtained by X-ray CT imaging, using a cone beam, of a first living organ and a second living organ which are symmetrically located with respect to a predetermined plane; and
a display part for arranging said CT image of said first living organ and said CT image of said second living organ which are acquired by said CT image acquisition part, on one display screen for comparison and displaying said CT image of said first living organ and said CT image of said second living organ with three cross-sectional planes which are orthogonal to one another.

5. The medical X-ray CT image display device according to claim 4, further comprising:
a storage part for storing said CT image of said first living organ and said CT image of said second living organ which are displayed for comparison while associating said CT images with each other,
wherein said display part displays said CT images of said first living organ and said second living organ which are stored in said storage part and associated with each other, for comparison.

6. The medical X-ray CT image display device according to claim 4, wherein when said display part specifies an imaging region of one of said first living organ and said second living organ and displays an arbitrary cross sectional CT image thereof, said display part also automatically displays a corresponding cross sectional CT image of the imaging region of the other living organ, which is located symmetrically to the specified imaging region with respect to said predetermined plane, on the same display screen for comparison.

7. The medical X-ray CT image display device according to claim 6, wherein said display part displays arbitrary said three cross-sectional planes are set with respect to each of said CT images of said first living organ and said second living organ and cursors associated with said three cross-sectional planes of each of said CT images, and by moving one of said cursors in any one of said three cross-sectional planes of one of said first and second living organs, said display part also moves said cursors in said three cross-sectional planes of the other living organ symmetrically with respect to said predetermined plane and displays a cross sectional CT image obtained at the position of said cursor with respect to each of said first living organ and said second living organ.

8. The medical X-ray CT image display device according to claim 4, wherein said first living organ and said second living organ are temporomandibular joints or otolaryngological regions.

9. The medical X-ray CT image display device according to claim 4, wherein said CT images of said first living organ and said second living organ are cross-sectional plane images at positions in plane symmetry with respect to said predetermined plane or images in a direction of mirror symmetry with respect to said predetermined plane.

10. The medical Xray CT image display device according to claim 4, wherein a CT image is synthesized by combining respective CT imaging data of said first living organ and said second living organ and CT imaging data of a third living organ located between said first living organ and said second living organ and displayed.

* * * * *